US007011659B2

(12) United States Patent
Lewis et al.

(10) Patent No.: US 7,011,659 B2
(45) Date of Patent: Mar. 14, 2006

(54) CONNECTOR FOR ATTACHING AN ALIGNMENT ROD TO A BONE STRUCTURE

(76) Inventors: Edward L. Lewis, 72 Oakview Ave., Maplewood, NJ (US) 07040; Roy M. Nuzzo, 977 Lawrence Ave., Westfield, NJ (US) 07090

( * ) Notice: Subject to any disclaimer, the term of this patent is extended or adjusted under 35 U.S.C. 154(b) by 307 days.

(21) Appl. No.: 10/388,471

(22) Filed: Mar. 17, 2003

(65) Prior Publication Data

US 2004/0186472 A1 Sep. 23, 2004

(51) Int. Cl.
*A61B 17/58* (2006.01)
(52) U.S. Cl. ........................................ 606/61
(58) Field of Classification Search .............. 606/61; 623/17.11
See application file for complete search history.

(56) References Cited

U.S. PATENT DOCUMENTS

| | | | |
|---|---|---|---|
| 4,269,178 A | 5/1981 | Keene |
| 4,289,124 A | 9/1981 | Zickel |
| 4,347,845 A | 9/1982 | Mayfield |
| 4,411,259 A | 10/1983 | Drummond |
| 4,611,581 A | 9/1986 | Steffee |
| 5,000,165 A | 3/1991 | Watanabe |
| 5,005,562 A | 4/1991 | Cotrel |
| 5,007,909 A | 4/1991 | Rogozinski |
| 5,413,576 A | 5/1995 | Rivard |
| 5,415,659 A | 5/1995 | Lee et al. |
| 5,429,639 A | 7/1995 | Judet |
| 5,476,462 A | 12/1995 | Allard et al. |
| 5,584,832 A | 12/1996 | Schlapfer |
| 5,630,817 A | 5/1997 | Rokegem et al. |
| 5,643,259 A | 7/1997 | Sasso et al. |
| 5,928,233 A | 7/1999 | Apfelbaum et al. |
| 6,074,393 A | 6/2000 | Sitoto |
| 6,077,263 A | 6/2000 | Ameil et al. |
| 6,090,111 A | 7/2000 | Nichols |
| 6,132,464 A | 10/2000 | Martin |
| 6,287,308 B1 | 9/2001 | Betz et al. |
| 6,352,537 B1 | 3/2002 | Strnad |
| 6,387,097 B1 | 5/2002 | Alby |

FOREIGN PATENT DOCUMENTS

FR 2642642 8/1990

*Primary Examiner*—Eduardo C. Robert
*Assistant Examiner*—Michael B. Priddy
(74) *Attorney, Agent, or Firm*—Patton Boggs LLP

(57) ABSTRACT

A connector for a spinal alignment system includes a base, a hook, a guide aperture, and a locking portion. The base includes a channel extending therethrough to receive a fixation rod. The hook extends from the base. The guide aperture is adapted to receive a bone fastener and the locking portion is adapted to engage the bone fastener. The guide aperture extends through one of the base and the hook and the locking portion is located in the other of the base and the hook. The locking portion is coaxial with the guide aperture such that the guide aperture guides a shaft of the bone fastener into alignment with the locking portion when the bone fastener is received by the guide aperture. The bone fastener cooperates with the base and hook to form a tension band construct that resists opposing forces acting on the construct. A rod locking fastener engages the channel and the fixation rod to secure the fixation rod in the channel.

8 Claims, 17 Drawing Sheets

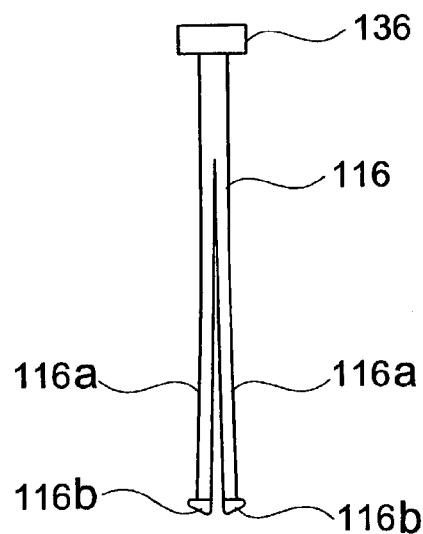
FIG.16
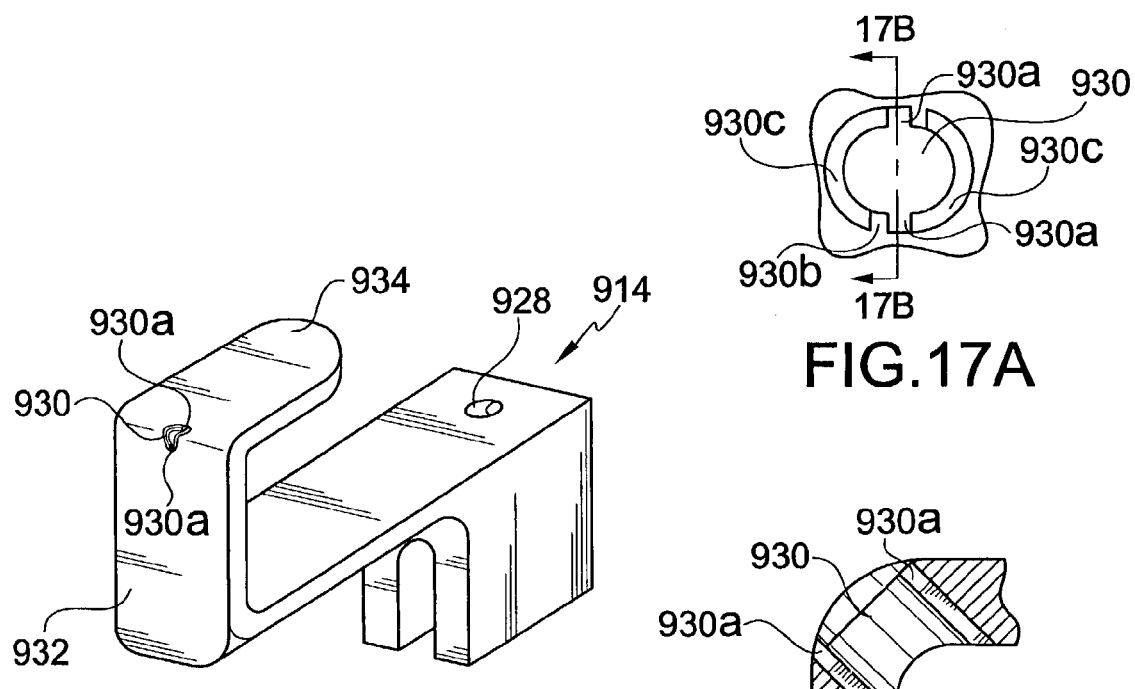
FIG.17
FIG.17A
FIG.17B

CONNECTOR FOR ATTACHING AN ALIGNMENT ROD TO A BONE STRUCTURE

BACKGROUND OF THE INVENTION

1. Field of the Invention

The invention relates generally to a spinal alignment system for treating spinal deformities and/or injuries and, more particularly, to securing a spinal alignment system to a spinal column.

2. Description of the Related Art

Deformities of the spine and injuries to the spine have long been treated by surgical intervention. In treating deformities and injuries to the spine, the goal is to return the spine, to the extent possible, back to a normal curvature and/or hold it in a desired position. Several surgical intervention techniques and devices have been proposed for the treatment of injuries to and deformities of the spine.

Some of these surgical techniques use a hook and rod system to hold the spine in a desired position. In such systems, the rod can be placed along the outside of the curved spine, that is on the convex side, and can be attached to the vertebrae of the spine by hooks as illustrated in FIG. 1. Because the rod is applying a generally compressive force along the spine to urge it into the desired position, this can be referred to as the compressive mode. Alternatively, a rod placed on the inside of the curved spine, that is on the concave side, would apply a generally tensile force along the spine to urge it into the desired position, which can be referred to as the distraction mode.

The device shown in FIG. 1 is an example of one of the first such systems referred to as a Harrington Instrumentation in the compression mode. With this device the rod is threaded (threads not shown) and can be straight or bent into a curvature that will place the spine in the desired position. Each hook is threaded onto the rod and secured to the rod by nuts and is frictionally seated on each vertebra. After all the hooks have been frictionally seated on the vertebrae and secured to the rod, the excess rod can be cut off. In the compression mode, the middle of the rod is pushing the spine to the desired position and the ends of the rod are pulling the spine to the desired position. This pulling force at the ends of the rod can be of such magnitude that the hook and rod system can fail. Depending upon the force, the hooks can pull or slip off because the hooks are open ended. Regardless, the desired position of the spine can be lost. Hook pull off and failure is not limited to the compression mode, it is also a problem in the distraction mode for this type of system. In addition, the ratcheted rods in the distraction mode could break at the ratchet points, again causing system failure.

To overcome problems with hooks pulling off the vertebrae, some devices attempted to secure the rod to the vertebrae with a screw screwed into the bone material instead of using a hook. The screw, however, is under perpendicular tension by the rod, thus, the pull on the screw is straight out of the bone along the screw's axis. With this construction, the screw is held in the bone only by the strength of its threads. Moreover, because the bone of the vertebrae is mostly cancellous and is relatively weak, it is not a preferred bone type for thread fixation. The weaker bone material is more likely to fail than the screw. As a result, the screws that are subject to the pulling forces described above can experience pull out and failure.

To avoid screw pull out due to bone failure, larger bone screws and larger threads have been used. But these larger features can disrupt too much of the vertebrae and cause the vertebrae to fracture, independent of screw pull out. Failures such as these can prevent further repair of the spinal column disorder unless there is additional surgery.

In a modification of the screw and rod system, the screws pass through plates that have slots or holes so that the screw can be oriented relative to the rod at an angle other than perpendicular to the rod. The slots or holes are configured to permit the angle of the screw relative to the rod to be selected from a range of angles. This modified orientation of the screw can reduce the load that the threads must support. However, the screw is still subject to failure by pull out and the threads can still cause the vertebra to fracture.

This effort to overcome problems experienced with screws led to a hook being used in combination with a screw. See, for example, U.S. Pat. No. 5,584,832. But use of both a hook and a screw does not eliminate the problems associated with each. The hook can still experience slippage and the screw can still experience pull out. In these devices, a hook frictionally engages the vertebra and a bone screw is passed into bone as well. Although these devices can provide for a more reliable mounting of the rod onto the spinal column over other devices, these devices, as stated above, cannot eliminate hook slippage and bone screw pull out. Also, this combination device requires a greater number of components for implantation as compared to the hook and rod systems and the bone screw systems discussed above.

In an effort to overcome problems experienced with screw pull out, a nut can be threaded on the far end of the screw. But nuts used on the far side of the screw in the spine are difficult to place and to hold until secure. The nut must be held blind on the side away from the incision. The screw needs to center in the nut, which requires palpation by the surgeon. The screw can be sharp, tearing gloves, exposing skin or even cutting the surgeon. Also, for the nut to relieve the screw threads from being the sole resistance force to pull out, the nut must be sufficiently tight against the bone, which is difficult to achieve by hand (without a holding device so that the nut does not spin while tightening is occurring). The use of a nut with the screw can be a difficult, cumbersome and time consuming procedure at best.

Furthermore, when using screws in spinal systems where the screw penetrates the vertebrae, with or without the use of a nut or hook, the screws must be accurately positioned on the vertebrae. This requires the use of some type of a jig or gauge or both. This holding device presets the target location for the screw to assure that the screws are precisely and accurately placed. A gauge is also used to measure the distance the screw should span, thus, avoiding over penetration beyond and into unintended tissues, and avoiding under penetration, which would mean fewer threads to resist pull out.

Accordingly, what is needed is an arrangement for securing a fixation rod of a spinal alignment system to the vertebra that is easy to install, yet is reliable and durable.

SUMMARY OF THE INVENTION

The invention solves the problems and/or overcomes the drawbacks and disadvantages of the prior art by minimizing the adverse effects of the tensile and compression forces acting on the various securements of the spinal alignment system. In particular, the invention accomplishes this by providing a connector for a spinal alignment system including a base, a hook, a guide aperture, and a locking portion. The base includes a channel extending therethrough to receive a fixation rod. The hook extends from the base. The guide aperture is adapted to receive a bone fastener and the locking portion is adapted to engage the bone fastener. The guide aperture extends through one of the base member and the hook member and the locking portion is located in the other of the base and the hook. The locking portion is coaxial with the guide aperture such that the guide aperture guides a shaft of the bone fastener into alignment with the locking portion when the bone fastener is received by the guide aperture.

There is also provided a rod locking fastener for securing a rod in a channel of a connector of a spinal alignment instrument, the rod locking fastener including a thread to engage the connector, an end to frictionally engage the rod and secure the rod to the connector, and a tool engagement portion adapted to receive a tool that drives the rod locking fastener into and out of engagement with the rod. The thread includes a first side extending from an adjacent root portion at a first acute angle. The end is adjacent to the thread.

There is also provided a spinal alignment system including a connector adapted to engage a vertebra of a human spinal column, a bone fastener, a fixation rod, and rod locking fastener. The connector includes a base having a channel, a hook extending from the base, a guide aperture extending through one of the base member and the hook member, and a locking portion being located in another one of the base member and the hook member, the locking portion being coaxial with the guide aperture. The bone fastener includes a head and a shaft extending from the head. The guide aperture cooperates with the shaft to guide the bone fastener through the vertebra in alignment with the locking portion when the bone fastener is inserted into the guide aperture. The locking portion engages the shaft after the bone fastener is inserted into the vertebra. The rod locking fastener cooperates with the channel to secure the fixation rod to the connector when the fixation rod is received in the channel.

In another aspect of the spinal alignment system, the system comprises a tension band. In particular, when the bone fastener is tightened in the locking portion, the bone fastener is placed in tension and the connector is placed in compression. As such, the bone fastener and the connector cooperate to define the tension band that distributes a force exerted by the fixation rod throughout the connector and the bone fastener.

In yet another aspect of the spinal alignment system, the rod locking fastener and the base include complimentary mating surfaces that are configured to resist the force exerted by the fixation rod onto the rod locking fastener when the fixation rod is secured in the channel.

There is also provided a fastener for securing a first component of an implant to a second component of the implant. The fastener includes a body extending along an axis and a thread disposed on and extending for a length along the body. The body has a first end and a second end opposing the first end. The thread includes an engagement portion and a root portion adjacent to and extending alongside the engagement portion. The engagement portion has a first face and a second face generally opposing the first face, wherein a first segment of the length of the thread has the first face disposed at an acute angle to an adjacent root portion.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide further understanding of the invention and are incorporated herein and constitute part of this specification, illustrate an embodiment of the invention, and, together with the general description given above and the detailed description given below, serve to explain the features of the invention.

FIG. 16 is a side view of an alternate embodiment of a bone fastener according to the present invention.

FIG. 17 is a perspective view of another embodiment of a connector according to the present invention with the connector being adapted for use with the bone fastener in FIG. 16.

FIG. 17A is an enlarged detail view of a portion of FIG. 17.

FIG. 17B is a cross-sectional view taken along line 17B—17B of FIG. 17A.

DETAILED DESCRIPTION OF THE PREFERRED EMBODIMENT

Figure 1:
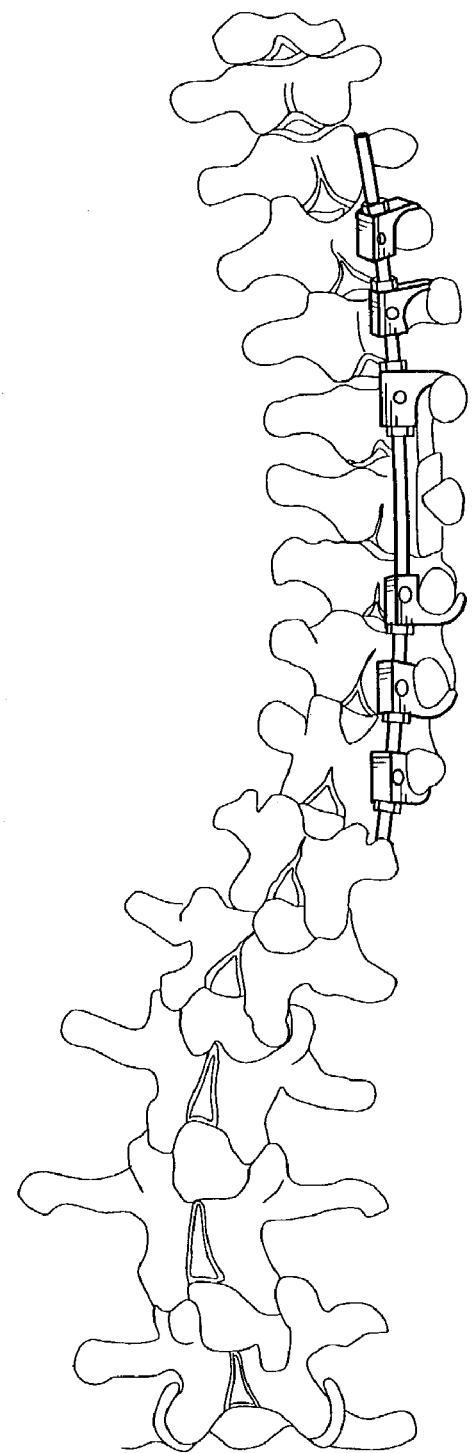
FIG. 1 is a posterior view of a human spinal column with a conventional Harrington Instrumentation (compression) spinal alignment system installed on the human spinal column.
Figure 2:
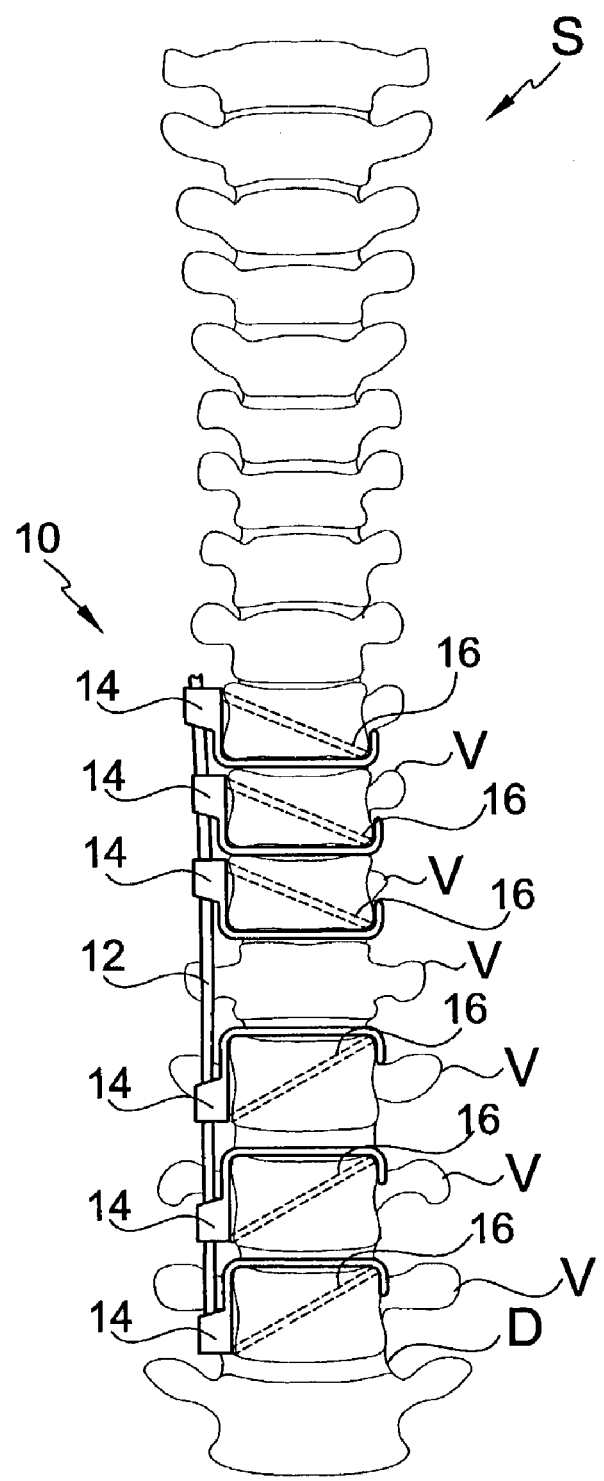
FIG. 2 is an anterior view of a human spinal column with a first embodiment of a spinal alignment system according to the present invention installed thereon.

The spinal alignment system 10 in accordance with the principles of the invention is shown generally by reference numeral 10 in FIG. 2. This spinal alignment system 10 can be used as an implantable system to correct abnormal curvatures and trauma to the spine. In FIG. 2, an anterior side of spinal column S is shown having the spinal alignment system 10 implanted on the anterior portion of the spinal column S, although posterior implantation can be performed. With posterior implantation the size of the system 10 would change, that is, it would be smaller because it would attach to the smaller bone structure on the posterior side of the spine. Although not shown with the inventive system 10, the posterior side of the spine is illustrated in FIG. 1 showing the smaller bone size. Spinal column S in FIG. 2 is illustrated in a corrected position having proper alignment in the coronal plane. However, not all corrective procedures will result in complete coronal alignment such that some curvature remains in the spinal column S after installation of the spinal alignment system 10.

Spinal alignment system 10 generally includes a fixation rod 12, connectors 14 and bone fasteners 16 and is shown attached to the vertebrae V targeted for correction. As discussed in more detail below, the fixation rod 12 is attached to the spinal column S by way of connectors 14 and bone fasteners 16. This allows the rod to correct and counterbalance the curve to be corrected or to hold the spinal column S in a more desirable alignment or position. In accordance with the principles of the invention, each connector 14 serves as both a bone fastener guide and a bone fastener locking mechanism, as well as a hook as discussed in more detail below. As such, system 10 more reliably prevents hook slippage, pull out from the bone, and breakage of components of the system 10 or of the spinal column S.

Figure 3:
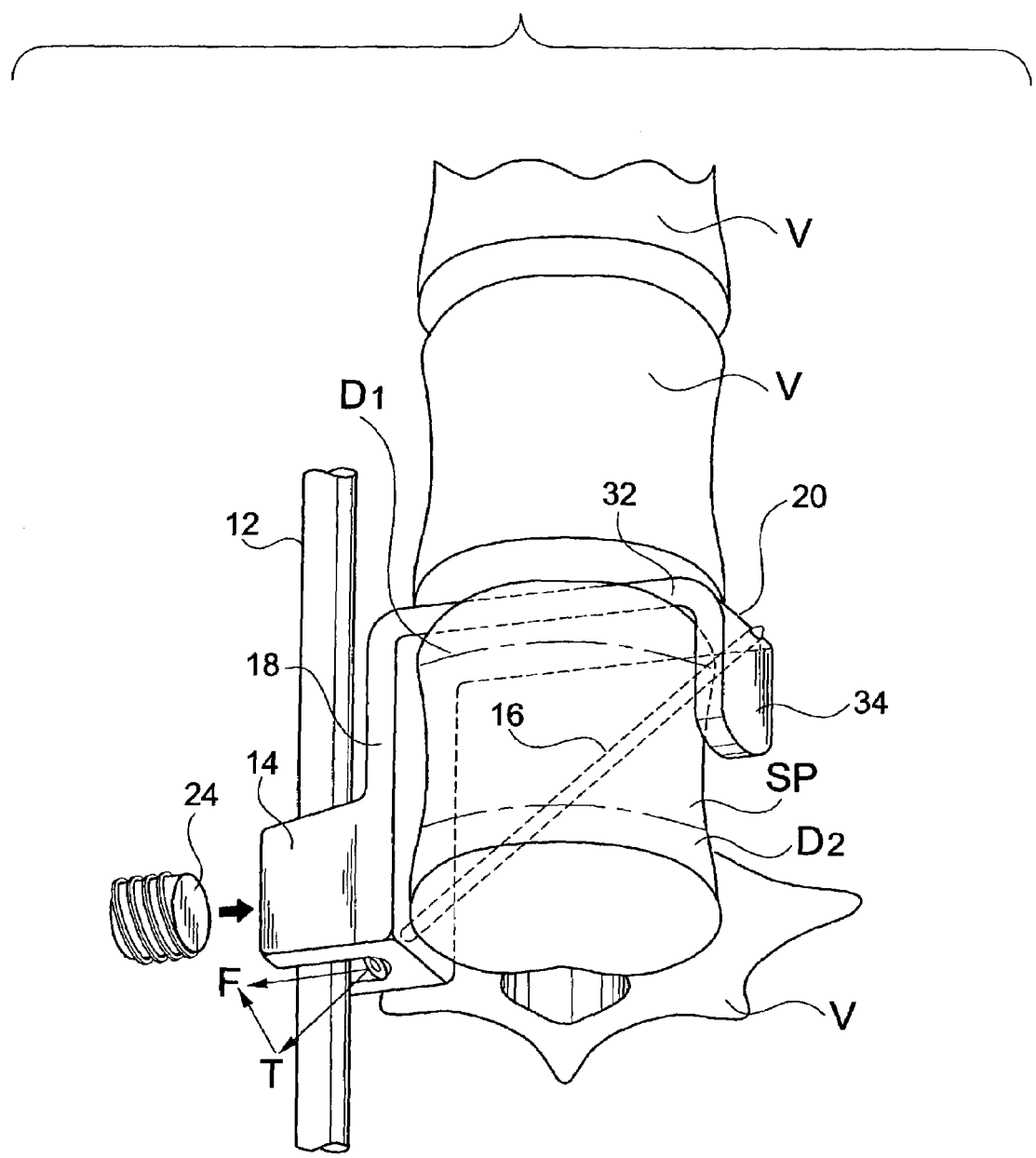
FIG. 3 is a perspective view of a portion of the spinal alignment system of FIG. 2.

Referring to FIG. 3, which shows an expanded view of one portion of the spinal fastening system 10 shown in FIG. 2, the details of system 10 will be described. The connector 14 is generally a C-shape having a base 18 adapted to receive and locate the fixation rod 12 and to receive and guide the bone fastener 16, and a hook 20 extending substantially perpendicular from the base 18 adapted to engage the vertebra V and adapted to receive and lock the bone fastener therein. The base 18 and fixation rod 12 extend along the length and on one side of the spinal column S. The hook 20 includes a first hook portion 32 and a second hook portion 34 disposed substantially perpendicular to the first hook portion 32. The first hook portion 32 is disposed between two vertebrae V. The disc D between the two vertebrae is removed to make space for the hook 20. The second hook portion 34 extends lengthwise and on the other side of the spinal column S from the fixation rod 12. Connector 14 can be made from a material suitable for implantation in the human body, such as, a suitable metallic material, including, for example, stainless steel, titanium, or cobalt chrome. In the following discussion, first the connector 14 and its attachment by bone fastener 16 will be described. Then the connector 14 and its attachment to the fixation rod 12 will be described.

As shown in FIG. 3, connector 14 is adapted to guide and lock the bone fastener 16 that extends from base 18 to hook 20. The details of this feature are henceforth described with reference to FIG. 5. Base 18 of connector 14 includes a guide aperture 28 extending therethrough. As shown, guide aperture 28 extends, preferably, obliquely through the base 18. The guide aperture 28 is sized to allow the bone fastener 16 to pass through it in a controlled manner. As shown, guide aperture 28 preferably is not threaded. Alternatively, the guide aperture 28 could be threaded. Hook 20 of connector 14 includes a threaded bore 30 extending therethrough and disposed coaxial with guide aperture 28. The threaded bore 30 has threads that are adapted to mate with the threads on bone fastener 16. As shown, the threaded bore 30 is disposed at the junction of the first hook portion 32 and the second hook portion 34. At this junction there is more material to pass through as compared to passing through the flat portions of the hook 20. Therefore, locating the threaded bore 30 at the junction allows for more threads as compared to other locations on the hook 20. When there are more threads to engage, the engagement force or lock down force maintaining the interconnection between the bone fastener 16 and the hook 20 is greater. Also, by positioning the threaded bore 30 at the junction, the length of the second hook portion 34 can be minimized. To facilitate entry of the bone fastener 16 into each of guide aperture 28 and the threaded bore 30, the inlet side of each of guide aperture 28 and threaded bore 30 can be tapered.

Figure 5:
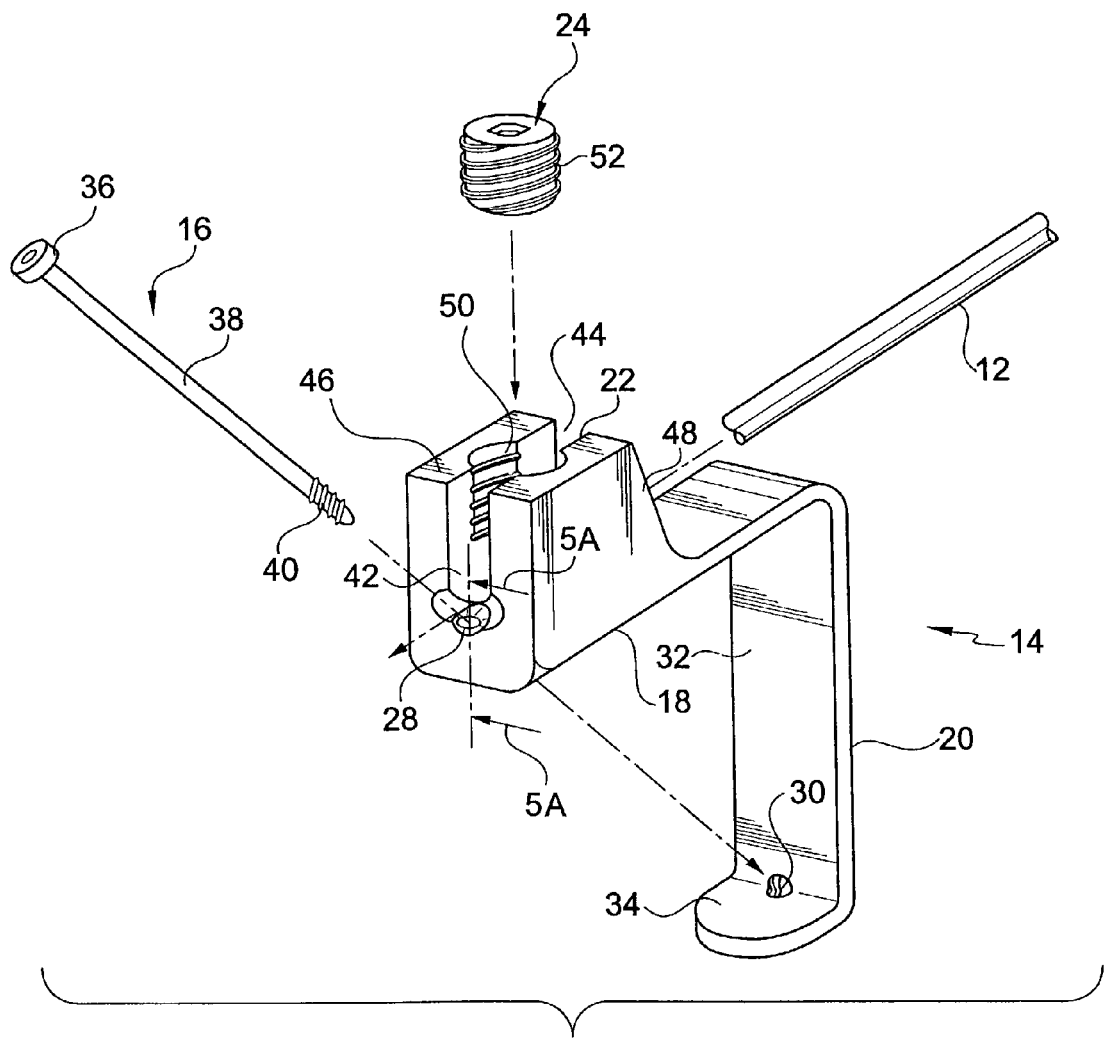
FIG. 5 is an exploded perspective view of the portion of the spinal alignment system shown in FIG. 3 and showing a different direction of view from that in FIG. 3.
Figure 5A:
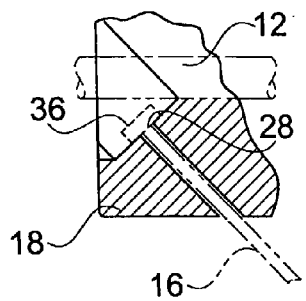
FIG. 5A is an enlarged partial cross-sectional view taken along line 5A—5A of FIG. 5.

The bone fastener 16, as shown in FIG. 5, has a head 36 at one end, a shaft 38 extending from the head 36, and threads 40 formed on the shaft 38 at the other end or tip of the bone fastener 16. Preferably, the bone fastener 16 is a bone screw having threads 40 only at the second end in a manner similar in design to a cancellous screw (used in the repair of bone fractures) or that of a typical bolt. Threads can be formed along any portion of the length of the bone fastener 16 if desired. Depending on the extent of the threads on the bone fastener 16, the guide aperture 28 may also be threaded. A dimple, detent or other similar structure can be provided at the second end of the bone fastener 16 to provided tactile input for the surgeon while threading the bone fastener 16 into the threaded bore 30, when threaded bore 30 is a through bore. In order to avoid puncturing the surgeon's gloves, or damaging adjacent tissue, the dimple, detent or other similar structure preferably is not sharp or pointed. Depending upon the size and shape of head 36, the guide aperture 28 can be formed with a complimentary receiving structure, such as a recess, so that the head 36 can be countersunk into the base 18 when the bone fastener 16 is in its final position. Depending upon the configuration, the recess can also function as the taper to guide the bone fastener 16 into the guide aperture 28. Furthermore, due to the increased strength of system 10, the size of the bone fastener 16 can be reduced as compared to bone screws currently in use by known spinal alignment/fixation devices. The bone fastener can be made from a material suitable for implantation in the human body, such as, a suitable metallic material, including, for example, but not limited to, stainless steel, titanium, or cobalt chrome.

Because the guide aperture 28 and threaded bore 30 are coaxial, the bone fastener 16 can be passed through guide aperture 28, through the vertebrae V and directly into alignment with the threaded bore 30. The threads 40 of the bone fastener 16 are threaded into threaded bore 30 until tight thereby securing the bone fastener 16 to the connector 14 to form a locking mechanism. Thus, the bone fastener 16 is locked into the hook 20, rather than just the bone. The use of a separate nut is unnecessary. Because the end of the bone fastener 16 is screwed into the hook 20 of connector 14, the bone fastener is in tension causing the connector to be under compression. Because the bone fastener 16 is both attached to the hook 20 and is under tension, a tension band construct is formed, and the hook 20 can more reliably resist the pulling or distraction forces exerted by the fixation rod 12 (illustrated in FIG. 3 by vector F) and avoid being pulled off the vertebrae. Moreover, as stated above, the connector 14 and bone fastener 16 are rigidly linked and form a closed loop, i.e., the tension band construct, around a portion of the vertebrae. Accordingly, the distraction force of the fixation rod 12 is spread through the whole connector 14 and the bone fastener 16, unlike the known spinal alignment/fixation devices which focus the distraction force onto the free end of the hook and on the wide threads of the screws. Therefore, although preferred, the bone fastener 16 need not be under tension to resist pull out forces from the fixation rod 12. If the bone fastener 16 is attached to hook 20 in such a manner that bone fastener 16 is not under tension, pull out can still be avoided because the bone fastener 16 is secured to the hook 20 to form a closed loop or band around/through the bone.

Additionally, the preferred oblique orientation of the guide aperture 28 and the threaded bore 30 in connector 14, and thereby the oblique orientation of the bone fastener 16, further increases the resistance to pull out. As shown in FIG. 3, the oblique orientation of the bone fastener 16 is non-parallel to the distraction force F (FIG. 3) allowing the system 10 to resist pull out along the entire length of the bone fastener 16, as compared to the known systems which can have screws disposed in direct alignment with the distraction force and therefore rely solely on the threads of the bone screw to resist pull out. Furthermore, the tensile force along the axis of the bone fastener 16, illustrated by vector T in FIG. 3, is non-parallel to the distraction force F such that the magnitude of the tensile force T is less than the magnitude of the distraction force F applied by the fixation rod 12. Thus, the bone fastener 16 can be smaller in size as compared to a bone screw used in known spinal alignment/fixation devices where the distraction force is the same.

Furthermore, because the connector 14 is used to guide the bone fastener 16 through the bone and to secure the bone fastener 16 on the other side of the bone, the use of a jig may be unnecessary. Additionally, no depth gauge is needed to judge the appropriate length of fastener 16 because fastener 16 is selected to match the length needed to bridge the distance between the guide aperture 28 and the locking bore 30. The coaxial alignment of guide aperture 28 and threaded bore 30 insures that the bone fastener 16 can be accurately, simply, and reliably secured to the connector 14.

The connector 14 can be provided in a plurality of different sizes to accommodate different sizes of vertebrae V. Selecting the proper size for the connector 14 ensures that the connector 14 is securely locked to the vertebra V. Moreover, different sizes of connector 14 can accommodate varying oblique orientations for the bone fastener 16. The size of connector 14 and orientations for the bone fastener 16 take into account the shape and size of the vertebra and the fact that the vertebra V is mostly cancellous, that is, the vertebra is composed of cancellous bone surrounded by a thin layer of cortical bone. Specifically, as shown in FIG. 3, the center portion SP of the vertebra is less dense, softer material than upper and lower portions D1, D2, which are stronger material. Because portions D1 and D2 are stronger, it is desirable to size the connector 14 and angle the orientation of the bone fastener 16 to take advantage of the denser, stronger parts of the vertebrae as illustrated in the embodiments disclosed herein. The system 10, however, can pass through only the softer portion SP of boney material, but it would not offer the same strength as having the system 10 pass through the denser portions of the vertebra.

But, the length for each of the base 18, the first hook portion 32 and the second hook portion 34 preferably are dimensioned to ensure that the bone fastener 16 extends through the vertebra V and, more preferably, through the dense bone portions D1, D2. Due to the make-up of the bone material, it is preferable to have the bone fastener extend obliquely through the vertebrae V to take advantage of the dense portions D1 and D2, however, any orientation can be used in accordance with the principles of the invention, including extending only through the center portion SP bone material.

In summary, the bone fastener 16 is dimensioned, oriented and secured to the vertebra V by way of connector 14 in such a manner to enhance the reliability and durability of the engagement of the bone fastener 16 with the vertebra V. Specifically, the bone fastener 16 can be oriented to extend through the strongest portion of the vertebra V, the bone fastener 16 is misaligned relative to the distraction force F applied by the fixation rod 12 to the bone fastener 16, and the threads on the bone fastener 16 engage metal, namely, connector 14, instead of only bone, thus the size and number of threads on the bone fastener 16 can be minimized. Further, the connector 14 is locked into engagement with the vertebra V. Simultaneously, the cross-sectional dimension, orientation, and securement of the bone fastener 16 minimizes injury (potential fracture) to the bone imparted by the bone fastener 16.

During installation, preferably, the bone fastener 16 is driven/tapped through the selected vertebra V without drilling a pilot hole owing to the porosity of the bone material of the selected vertebra V. The guide aperture 28 properly aligns the bone fastener 16 as it is inserted through the vertebra V such that the bone fastener 16 passes obliquely from the base 18 through the vertebra and threads into the hook 20 to secure the connector 14 to the vertebra V. If necessary, a hole can be drilled, or tapped, partially or completely, through the vertebra V to facilitate the passage of the bone fastener 16 through the vertebra. If a hole is to be formed in the vertebra V, then the boring tool to be used to form the hole should be positioned on the vertebra such that the hole will be properly aligned coaxially with the guide aperture 28 and the threaded bore 30. For example, the boring tool could be placed in a jig, which is a device that directs the boring tool through the bone and prevents the boring tool from drilling through the bone and into tissue surrounding the bone. Depending upon the boring tool, the connector 14 could be used for alignment, but a jig still might be desirable for this step.

Figure 4A:
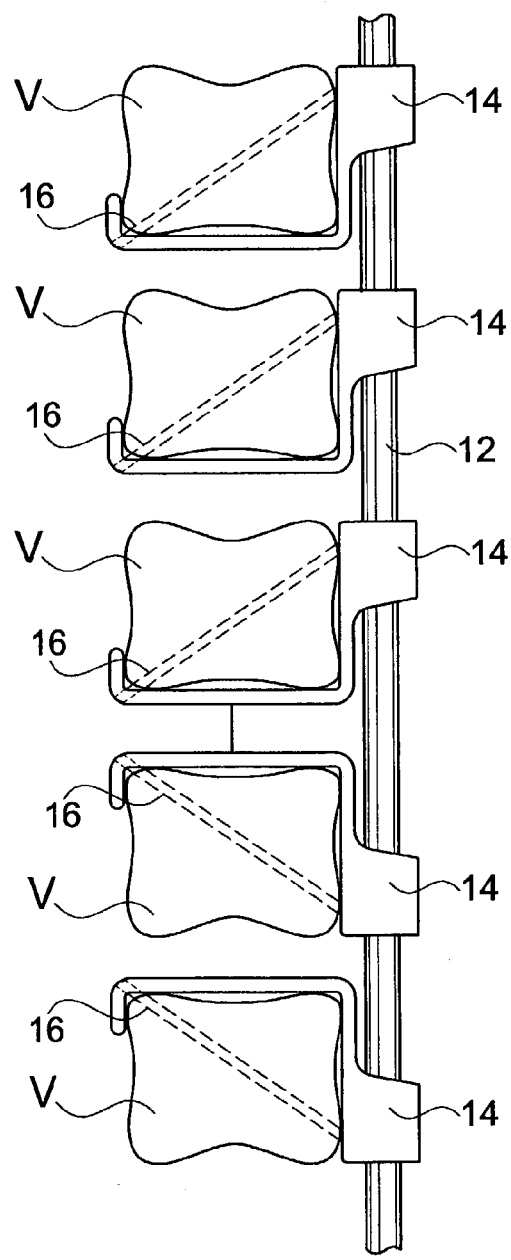
FIGS. 4A and 4B are schematic views showing various alternative arrangements of the spinal alignment system in accordance with the principles of the invention.
Figure 4B:
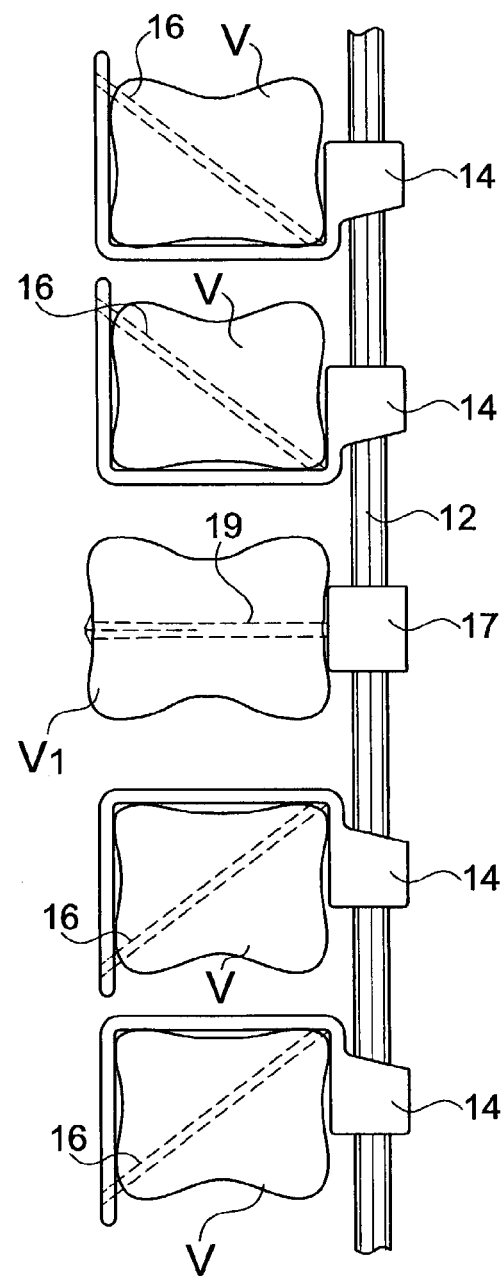

The arrangement of the connectors 14 and the bone fasteners 16 on the spinal column S can vary given the particular treatment. Two examples are shown in FIGS. 4A and 4B. The bone fasteners 16 can be arranged in a plurality of patterns that lock the connectors 14 to the vertebra V to promote a reliable and durable attachment of system 10 to the spinal column S. As shown by way of example in FIG. 4A, where the rod is disposed on the opposing side of the spine as compared to the rod in FIG. 2, the fasteners 14 are positioned on the vertebra V such that a first group of bone fasteners 16 converges towards a second group of bone fasteners 16. A further exemplary pattern is illustrated in FIG. 4B, where a first group of bone fasteners 16 diverges from a second group of bone fasteners 16. Also, the fasteners 16 and the hooks of the connectors 14 could be reversed with the hooks and fasteners pointed in the opposite directions from those shown in FIGS. 4A and 4B.

Additionally, FIG. 4B illustrates a bone anchor 17 secured to a vertebra VI by a bone fastener 19 that is oriented perpendicular to the fixation rod 12, where the vertebra VI is located approximately at the center of the arc of the spinal curvature being corrected. This bone fastener 19 serves to maintain proper positioning of its respective vertebra V relative to the fixation rod 12 and the adjacent vertebrae V. In the compression mode, due to the central position of the vertebra VI along the arc to be corrected, the fixation rod 12 applies a compressive force on the bone fastener 19 instead of the distraction or pulling force experienced at the ends of the fixation rod 12. As such, pull out of the bone fastener 19 is believed to be unlikely because of the connection of connectors 14 and bone fasteners 16 on either side of the bone fastener 19. The bone fastener 19 can be configured such as that shown and described below with reference to FIG. 16. Alternatively, the bone fastener 19 can be a smooth pin, a screw, a bolt or a staple extending from the bone anchor 17.

Now the attachment of the connector 14 to the fixation rod 12 and the fixation rod will be discussed. The connector 14 is adapted to have the fixation rod 12 secured thereto such that the fixation rod 12 is oriented relative to the selected vertebrae V to place the spine in the desired position to correct an abnormal curvature, or to position the spine for an operative procedure addressing a tumor, bone fracture, or other trauma to the spine. As shown in FIG. 5, the connector 14 includes a channel 22 formed in the base 18 of the connector 14 that is adapted to receive fixation rod 12. The channel 22 has a first open end 42 and a second open end 44. The bottom of the channel 22 has a shape complimentary to the shape of the fixation rod 12. Preferably, as shown in FIG. 5, the bottom of the channel 22 is cylindrical and the fixation rod 12 is cylindrical. The channel 22 forms two parallel side walls 46, 48 that extend from the first open end 42 to the second open end 44 of the channel 22. Each of the side walls 46, 48 includes a threaded portion 50 that engages threads 52 on the rod locking fastener 24 such that the rod locking fastener 24 can be tightened against the fixation rod 12 to secure the fixation rod 12 in the channel 22. The threaded portions 50 are segments of a thread helix but because the channel 22 extends through the thread helix it divides the thread helix into the two threaded portions 50. Preferably, the rod locking fastener 24 is a set screw having a flat end that engages the fixation rod and a driving end that is configured for engagement by a standard tool, such as a hex head screw driver. The rod locking fastener 24 and the base 18 of connector 14 can be structurally modified to further reduce the chances that the fixation rod 12 may disengage from the connector 14, as will be discussed below with reference to FIGS. 11A–13. Also, the outer surface of the walls 46, 48 can extend parallel, at a congruent angle, or divergent to one another.

The fixation rod 12 can be of any geometric shape in transverse cross-section, such as circular or polygonal. Preferably, the fixation rod 12 is solid and has a circular transverse cross-section with a diameter in the range of approximately ⅛ to ¼ inch. The fixation rod 12 may be straight or curved along its long axis. It is preferred to use a curved fixation rod 12 when treating kyphosis or lordosis or similar conditions of the spinal column. The fixation rod 12 can be made from a pliable material such that it can be bent to the proper shape by the surgeon during the operation but will retain its properly bent shape after implantation onto the spinal column S. The fixation rod is made from a material acceptable for implantation in a human body, such as stainless steel, titanium, cobalt chrome, or a composite material. The rod can be made as a solid member or made of strands that are woven, twisted, or welded into the appropriate shape and size.

In summary, the spinal alignment system 10 can be implanted by removing the discs between the vertebra V targeted for correction. The connectors 14 are then installed transversely across the vertebral disc spaces and secured to the vertebra V by respective bone fasteners 16. The fixation rod 12 is then inserted into each channel 22 of the connectors 14 in the desired corrective alignment and a rod fixation fastener 24 is then threaded into the threaded portions 50 of the channel 22 of each of the connectors 14. Typically, bone graft material is packed into the residual disc spaces. Bone induction material can also be used as, ultimately, bone fusion of the selected vertebrae V must be obtained. The spinal alignment system 10 according to the invention is not a substitute for bone continuity. Spinal correction devices, like spinal alignment system 10, are intended to temporarily hold the bones in the selected alignment until bone fusion occurs. Solid bone fusion must occur for spinal correction devices, like spinal alignment system 10, to achieve their intended goal.

Figure 6A:
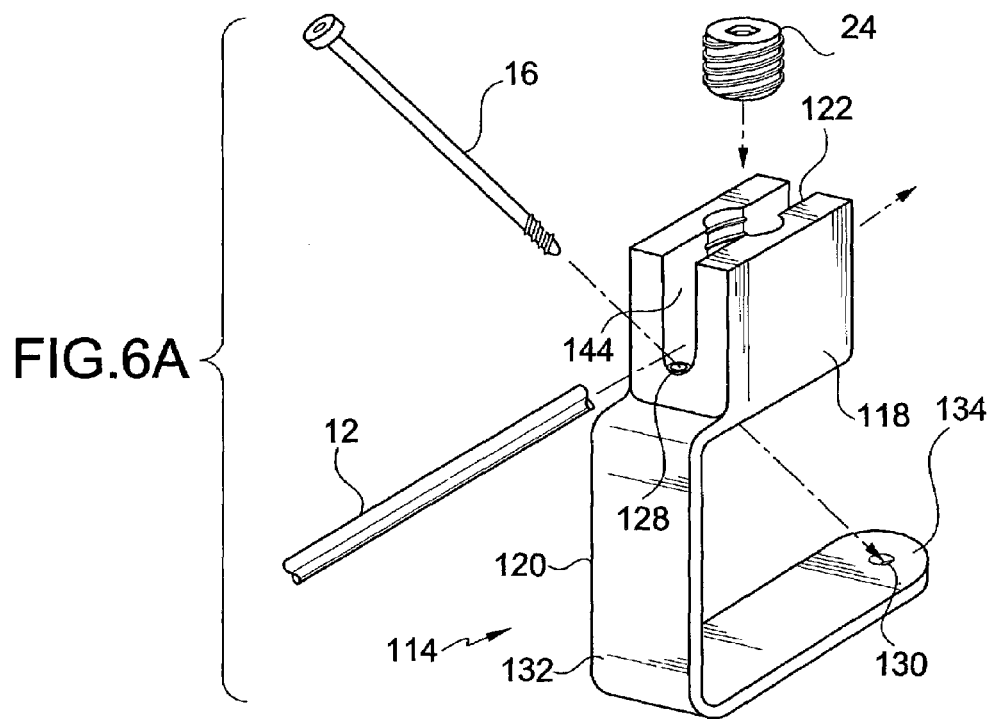
FIGS. 6A–6F are perspective views of alternate embodiments of the components of the spinal alignment system according to the present invention.

As discussed above, the bone fastener 16 can be disposed at any angle and can pass through different parts of connector 14. Examples of alternative embodiments in this regard are now described with reference to FIGS. 6A–6F. In FIG. 6A, a second embodiment of a connector 114 includes a base 118 and a first portion 132 of a hook 120 extending from the base 118 adjacent the second open end 144 of a channel 122 formed in the base 118. A guide aperture 128 extends through the channel 122 adjacent the second open end 144 of the channel 122. A second hook portion 134 extends from the first hook portion 132 and is longer as compared to the second hook portion 34 of the connector 14, as illustrated in FIGS. 2–5. A threaded bore 130 is located adjacent the free end of second hook portion 134 of the hook 120.

Figure 6B:
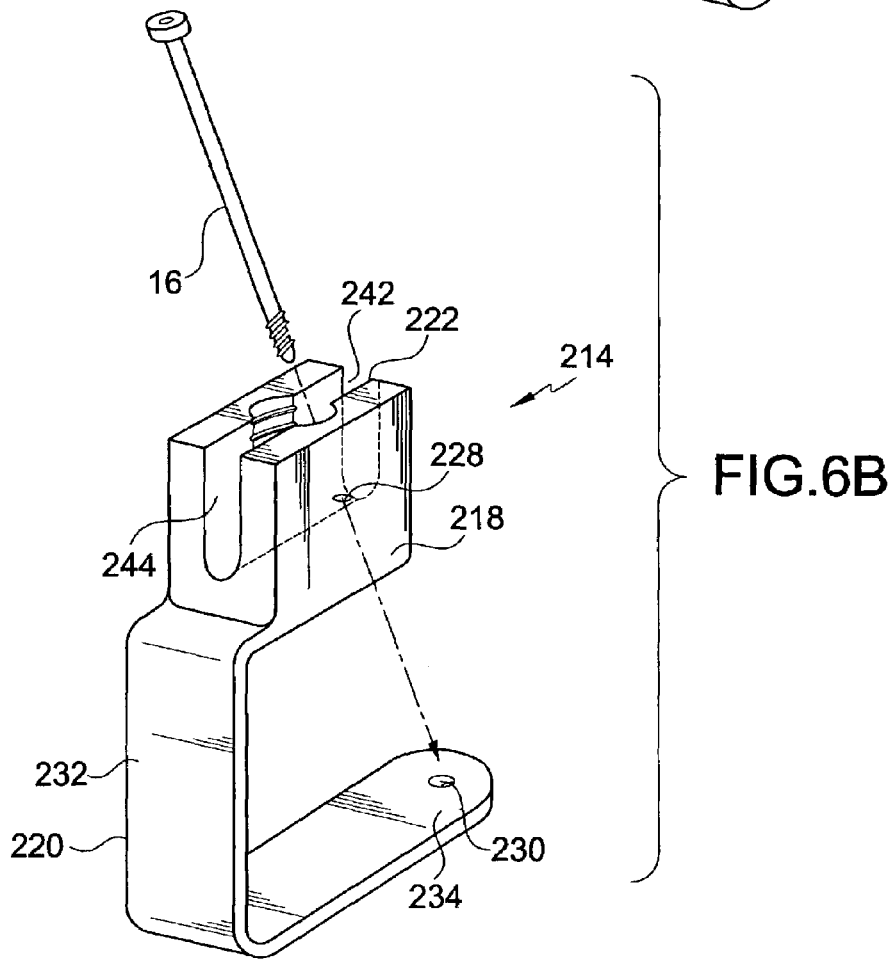

FIG. 6B illustrates a third embodiment of the connector 214 including a base 218 and a first portion 232 of a hook 220 extending from the base 218 adjacent the second open end 244 of a channel 222 formed in the base 218. A second hook portion 234 extends from the first hook portion 232 and is longer as compared to the second hook portion 34 of the connector 14, as illustrated in FIGS. 2–5. The connector 214 includes a guide aperture 228 extending through the channel 222 adjacent the first open end 242 of the channel 222 and a threaded bore 230 adjacent the free end of the second hook portion 234 of the hook 220. The bone fastener 16 is inserted through the guide aperture 228 and threaded into the threaded bore 230.

Figure 6C:
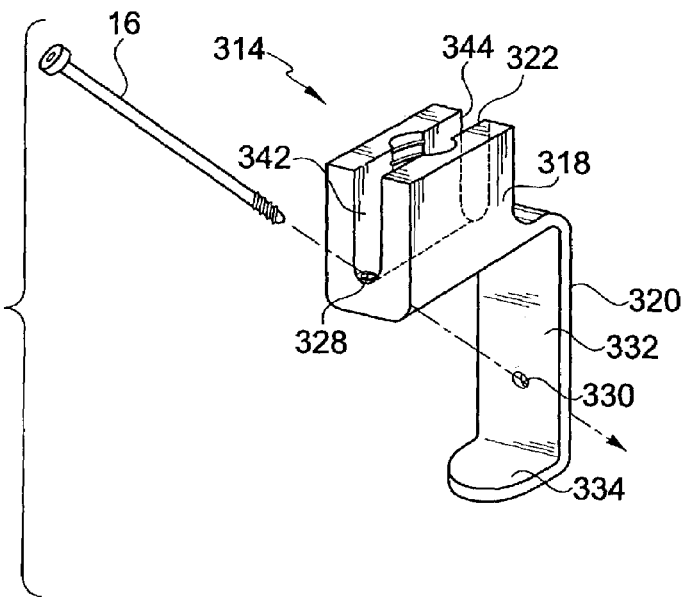

FIG. 6C illustrates a fourth embodiment of the connector 314. Like the first embodiment of FIGS. 2–5, the connector 314 includes a base 318 and a first portion 332 of a hook 320 extending from the base 318 adjacent the second open end 344 of a channel 322 formed in the base 318. A guide aperture 328 extends through the channel 322 adjacent the first open end 342 of the channel 322. A second hook portion 334 extends from the first hook portion 332. The threaded bore 330 is located in the first hook portion 332 of the hook 320 intermediate the second hook portion 334 and the base 318.

Figure 6E:
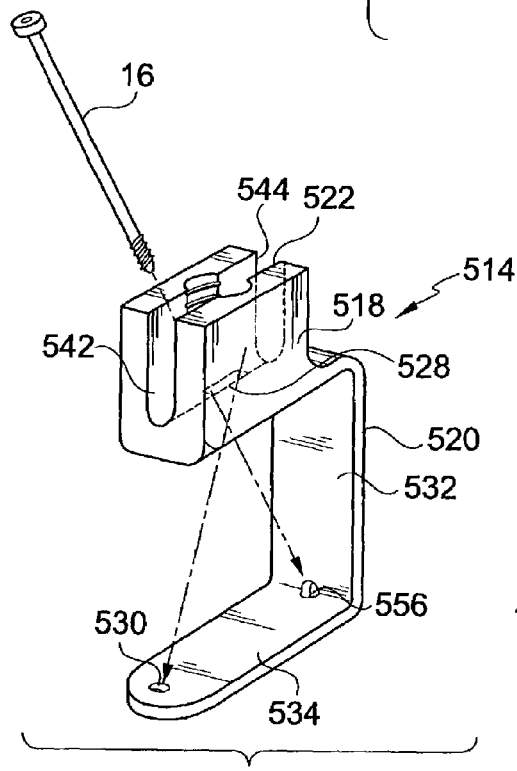
Figure 6D:
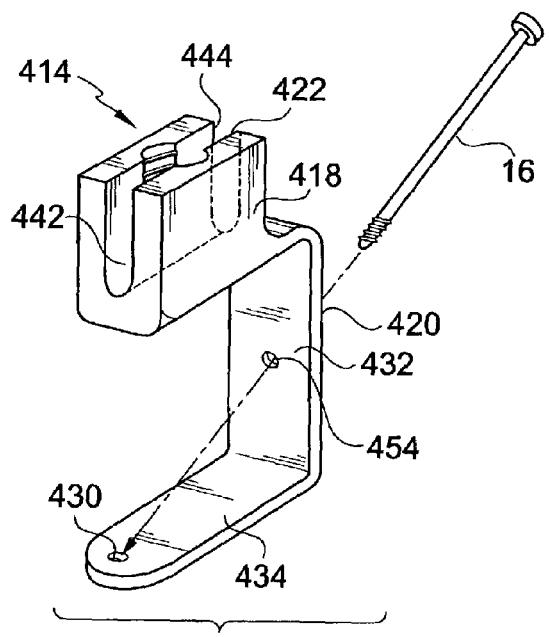

FIG. 6D illustrates a fifth embodiment of the connector 414. The connector 414 includes a base 418 and a first portion 432 of a hook 420 extending from the base 418 adjacent the second open end 444 of a channel 422 formed in the base 418. A guide aperture 454 extends through the first hook portion 432. A second hook portion 434 extends from the first hook portion 432 and is lengthened compared to the second hook portion 34 of the connector 14, as illustrated in FIGS. 2–5. A threaded bore 430 is located adjacent the free end of the second hook portion 432 of the hook 420. The bone fastener 16 is inserted through the guide aperture 454 and threaded into the threaded bore 430.

FIG. 6E illustrates a sixth embodiment of the connector 514. The connector 514 includes a base 518 and a first portion 532 of a hook 520 extending from the base 518 adjacent the second open end 544 of a channel 522 formed in the base 518. An elongated guide aperture 528 extends through the channel 522 at a location intermediate the first open end 542 and the second open end 544 of the channel 522. Preferably, the elongated guide aperture 528 tapers from the bottom portion of the channel toward the second hook portion 534 such that the end of the guide aperture 528 closest to the second open end 544 directs the shaft of the bone fastener 16 toward the first threaded bore 530 and the end of the guide aperture 528 furthest from the second open end 544 directs the shaft of the bone fastener 16 toward the second threaded bore 556. A second hook portion 534 extends from the first hook portion 532 and is lengthened compared to the second hook portion 34 of the connector 14, as illustrated in FIGS. 2–5. A second threaded bore 556 is located at the junction of the first hook portion 532 and the second hook portion 534 of the hook 520. One or more bone fasteners 16 can be inserted through the guide aperture 528 and threaded into either or both of the threaded bores 530, 556.

Figure 6F:
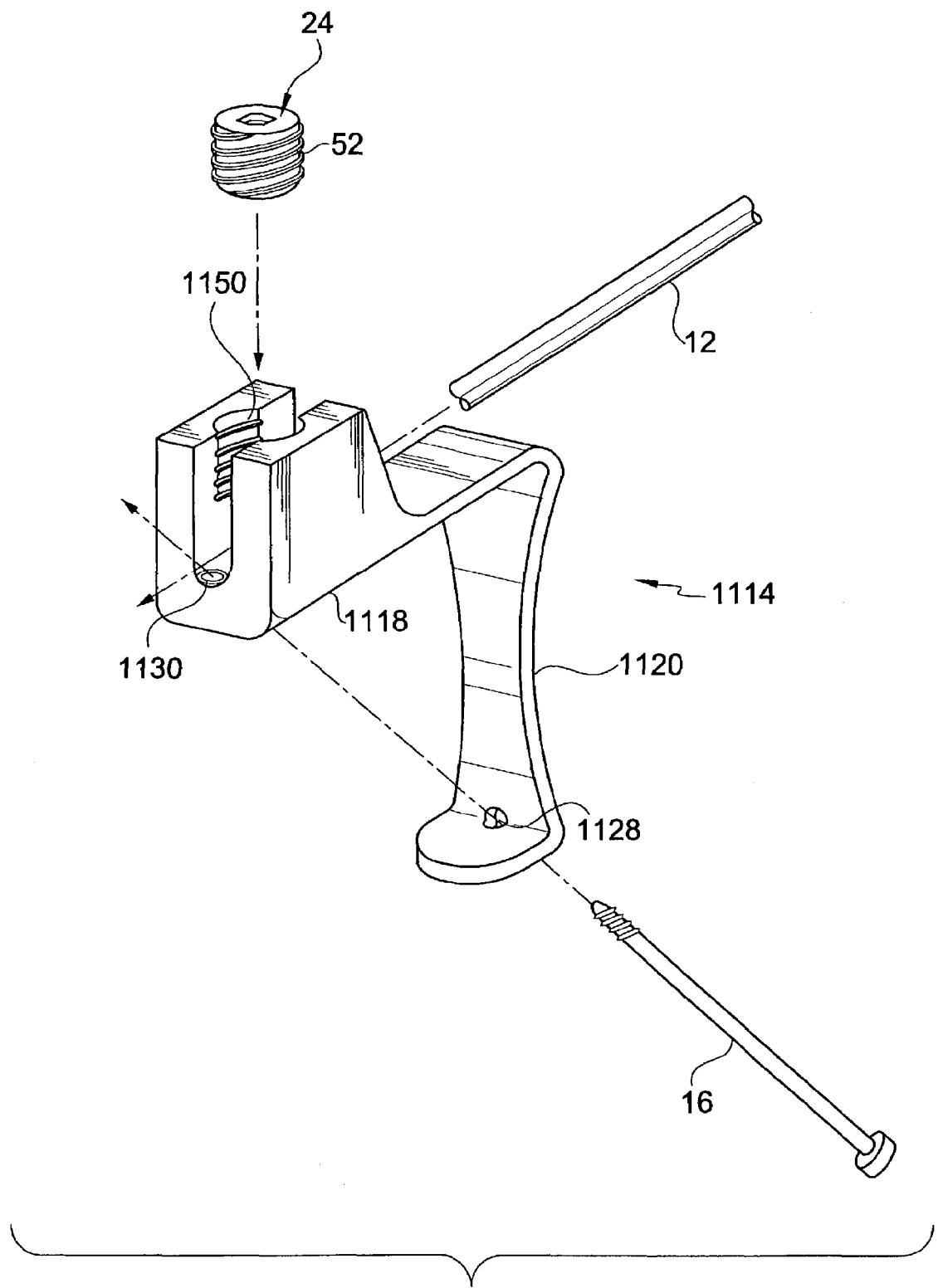

As described herein, the spinal alignment system in accordance with the principles of the invention can be implanted posterior to the spinal column. To implant the system posteriorly or anteriorly, the bone fastener insertion direction could be reversed as compared to that described above with reference to FIGS. 3, 5 and 6A–6E. That is, it could enter the connector through the hook first, as shown in FIG. 6F, rather than through the base first. As shown in FIG. 6F, a connector 1114 includes guide aperture 1128 located in the hook 1120 and a threaded bore 1130 located in the base 1118 of the connector 1114. The bone fastener 16 would enter into guide aperture 1128 and then be secured into the threaded bore 1130. Thus, in accordance with the principles of the invention, the various embodiments of the bone fastener illustrated in FIGS. 2–6F can be used for both a posterior implant and an anterior implant.

As described herein, the guide aperture is illustrated to open in the bottom of the channel and extend through the base along an axis that lies in a plane containing the longitudinal axis of the channel. However, the guide aperture can be positioned such that it opens in one of the side walls (for example side walls 46, 48 shown in FIG. 5) formed by the channel and extends through the base along an axis that is oblique to the plane containing the longitudinal axis of the channel.

As described herein, the first hook portion is illustrated with a constant width. However, the width of the first hook portion can be tapered inwardly, as shown in FIG. 6F, from each end of the first hook portion toward the middle of the first hook portion. This configuration can provide more area on the associated vertebra V for receiving bone graft material, thus maximizing the amount of the bone graft and the area of the vertebral surface to incorporate the graft.

Figure 7:
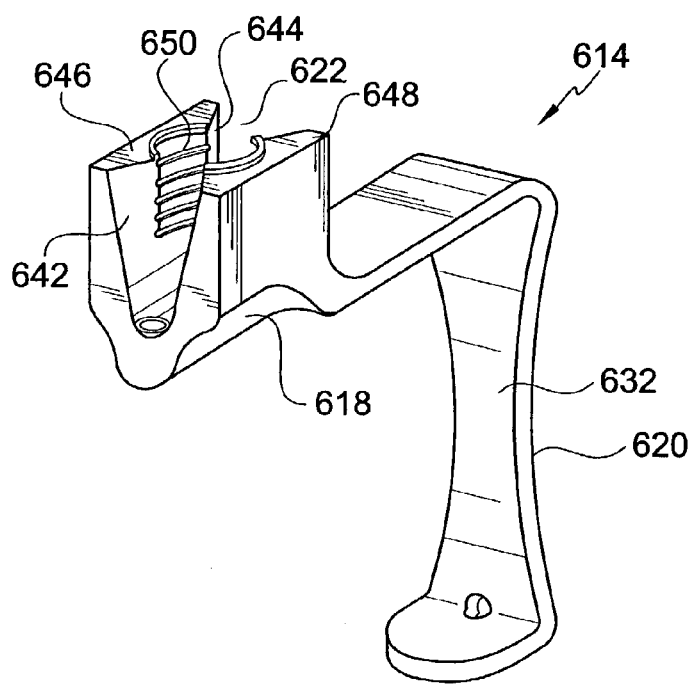
FIG. 7 is a perspective view of an alternate embodiment of a connector of a spinal alignment system according to the present invention.
Figure 7A:
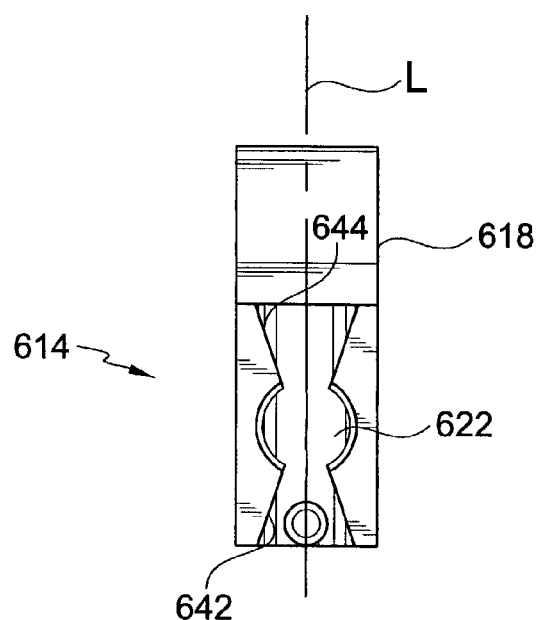
FIG. 7A is a plan view of the connector of FIG. 7.

In FIGS. 7 and 7A, a seventh embodiment of the connector 614 includes a base 618 and a hook 620 extending from the base 618. The base 618 includes a channel 622 having a tapered first open end 642 and tapered second open end 644. The tapered channel 622 is preferred over a straight channel, such as that illustrated in FIGS. 2–5. The tapered ends 642, 644 assist in guiding the fixation rod (not shown) during insertion into the channel 622 and they can more readily accommodate curved fixation rods and reduce the potential for edge loading. Also, the tapered ends 642, 644 reduce wear on the rod by providing a relatively dull edge upon which the fixation rod (not shown) can rub if the fixation rod should ever move within the channel 622. The angle of taper for the tapered ends 642, 644 can have a wide range, but is preferably between approximately 5–45 degrees as measured relative to longitudinal axis L in FIG. 7A.

The first hook portion 632 of the hook 620 has a tapered width to maximize the amount of bone graft and area of the vertebral surface to incorporate the bone graft, as also shown in FIG. 6F. Further, the base 618 can be configured differently. As shown in FIG. 7, the outer surface of the base 618 is sculpted in an area underneath the channel 622 and along a portion of the walls 646, 648 of the channel 622. The sculpted portions of the base 618 are configured to gradually transition from one end adjacent the first end 642 of the channel 622 toward the planar surface portion of the base 618 intermediate the second end 644 of the channel 622 and the hook 620. The sculpted portions of the base 618 provide an optimized distribution of material along the base 618 that can minimize the space in the spine to be occupied by the connector 614 and that can maximize the depth of the threaded portions 650 for the rod locking fastener (not shown, see, for example, FIG. 3). This also results in the use of less material as compared to other embodiments. FIGS. 7 and 7A illustrate the outer surface along the top portions of the walls 646, 648 as being parallel to one another and the outer surface along the bottom portions of the walls 646, 648 to be non-parallel to one another. The non-parallel extent of the outer surface along the bottom portions of the walls 646, 648 can have a divergent configuration, as shown in FIG. 7, or alternatively, a congruent configuration, as shown in FIG. 5, where a gradual transition is not used. Alternatively, the outer surface of the base can be sculpted along the entire extent of the walls 646, 648 in a divergent or congruent configuration.

Figure 8:
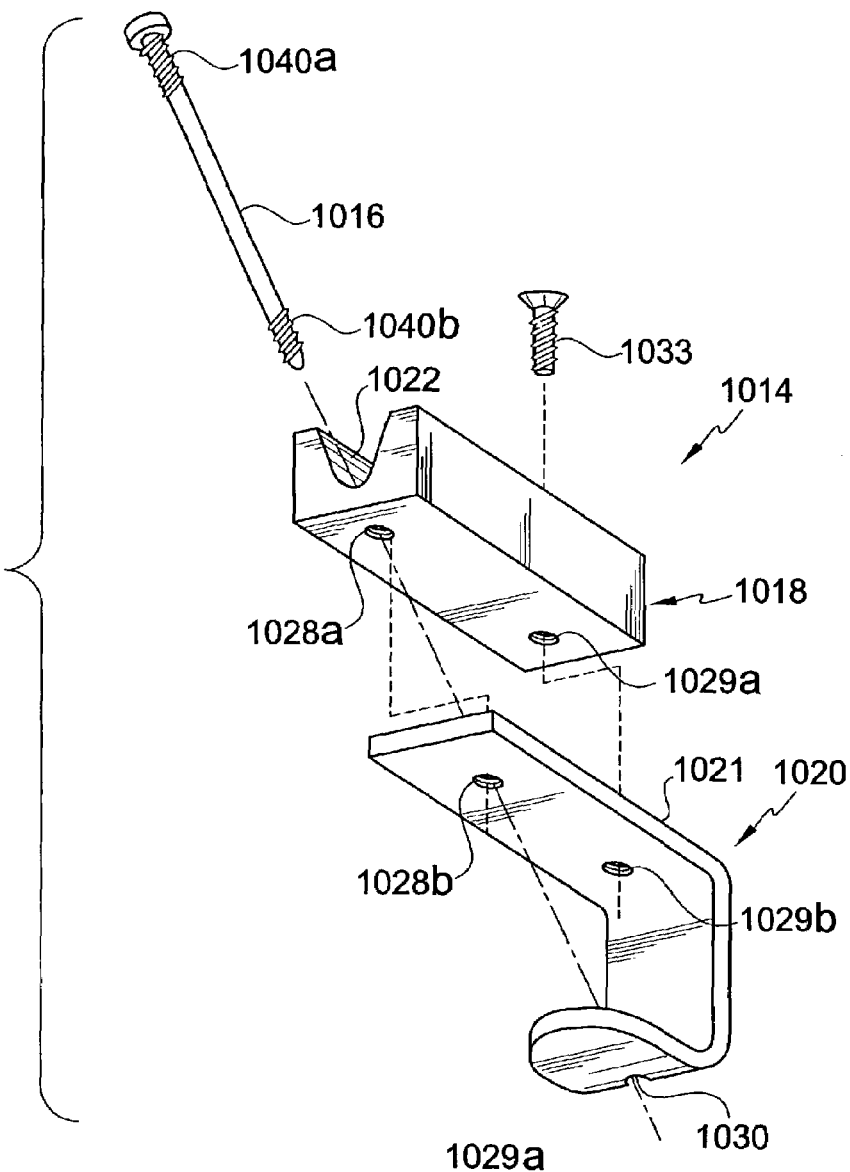
FIG. 8 is an exploded perspective view of another alternate embodiment of a connector of a spinal alignment system according to the present invention.
Figure 8A:
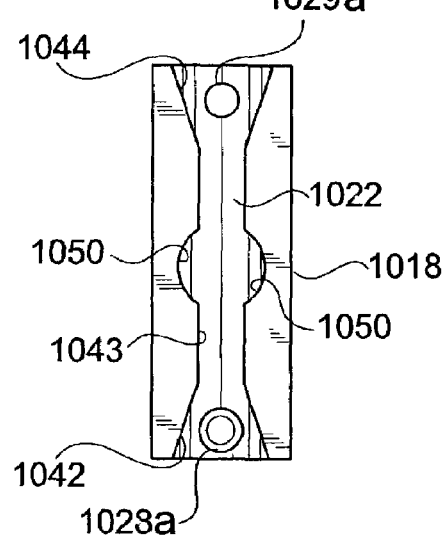
FIG. 8A is a plan view of the connector of FIG. 8.

FIGS. 8 and 8A illustrate two modifications as compared to the connector 14 of FIGS. 2–5. Referring to FIG. 8, the connector is a multi-piece connector 1014 that includes a base 1018 separable from a hook 1020. Providing the base 1018 as a separate component from the hook 1020, can enhance the ease of manipulation of the fixation rod (not shown) and the base 1018 into the desired alignment relative to the spinal column (not shown) because the base 1018 can be displaced relative to the hook 1020 and the hook 1020 can be rotated or moved along the vertebra V. A threaded fastener 1033 and a bone fastener 1016 are used to secure the base 1018 to the hook 1020 once the desired orientation is acquired.

The base 1018 includes a guide aperture 1028a that is threaded and a fastener bore 1029a. The hook 1020 includes a platform 1021 that receives the base 1018. A guide aperture 1028b and a fastener bore 1029b are provided in platform 1021 and align with the guide aperture 1028a and the fastener bore 1029a of the base 1018 when the base 1018 is placed on the platform 1021. At least one of the fastener bores 1029a, 1029b are threaded, and preferably, the fastener bore 1029b is threaded. The bone fastener 1016 has a first threaded portion 1040a to engage the threads in the threaded guide aperture 1028a and a second threaded portion 1040b to engage a threaded bore 1030 formed in the hook 1020. The threaded fastener 1033, preferably a flat head screw, is tightly threaded into the countersunk fastener bores 1029a, 1029b and cooperates with the bone fastener 1016 to secure the base 1018 to the hook 1020.

As viewed in FIG. 8A, the channel 1022 is lengthened as compared to the channel shown in FIGS. 2–7A. The channel 1022 has a tapered first open end 1042 and a tapered second open end 1044. The tapered ends 1042, 1044 merge into parallel sections 1043 that include threaded portions 1050, which receive a rod locking fastener (not shown). As discussed above relative to FIGS. 7 and 7A, the tapered ends 1042, 1044 assist in guiding the fixation rod (not shown) during insertion into the channel 1022 and they can more readily accommodate curved fixation rods and reduce the potential for edge loading. Also, the tapered ends 1042, 1044 reduce wear on the rod by providing a relatively dull edge upon which the fixation rod (not shown) can rub if the fixation rod should ever move within the channel 1022. The angle of taper for the tapered ends 1042, 1044 can have a wide range, but is preferably between approximately 5–45 degrees as measured relative to longitudinal axis L in FIG. 7A. Although FIGS. 8 and 8A illustrate the lengthened base in combination with a removable base, it is to be understood that these two modifications can be employed individually, as desired.

Figure 9:
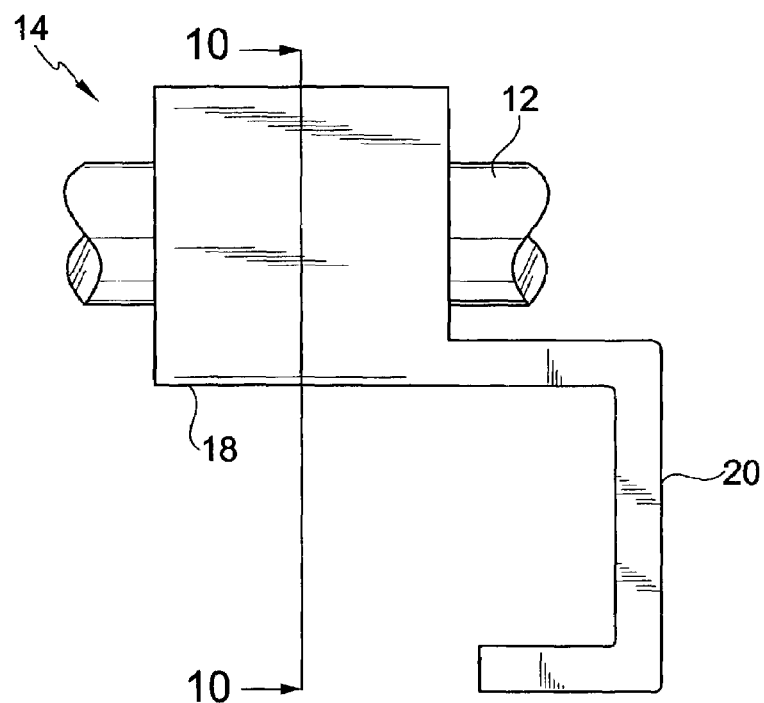
FIG. 9 is a side view of the spinal alignment system of FIG. 3 with the spinal column and the bone fastener omitted for clarity.
Figure 10:
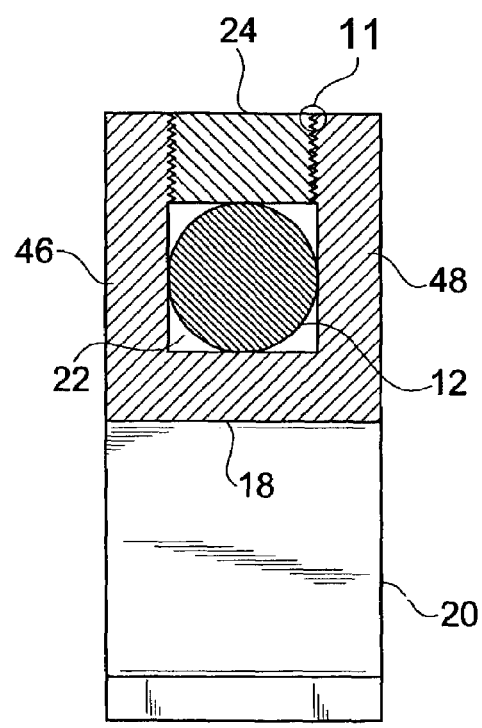
FIG. 10 is a cross-sectional view taken along line 10—10 of FIG. 9.
Figure 11:
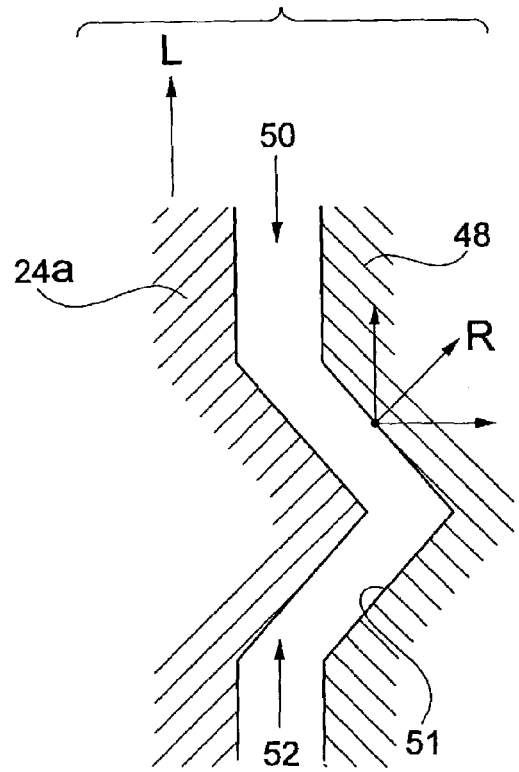
FIG. 11 is an enlarged view of Area 11 of FIG. 10 showing a first embodiment of the rod locking fastener thread configuration according to the present invention.

Turning now to FIGS. 9–11, the rod locking fastener 24, as illustrated in cross-section in FIG. 10, will be discussed in more detail. As shown in FIG. 10, the rod locking fastener 24 can have a conventional screw thread. In use, however, the fixation rod 12 can exert significant force on the rod locking fastener 24. To improve the reliability of the connection between the rod locking fastener and base, alternative thread constructions are described in comparison to a conventional screw thread. The alternative constructions are shown in FIGS. 11A–13.

FIG. 11 is an enlarged cross-sectional view indicated by Section 11 in FIG. 10 and shows a conventional V-shaped thread 52 extending along the body 24a of the rod locking fastener 24 and a conventional V-shaped thread 51 on the threaded portion 50. FIG. 11 illustrates the forces acting on the conventional V-shaped threads 51 of the threaded portions 50 of each of the side walls (only side wall 48 is shown) and the conventional V-shaped thread 52 of the rod locking fastener 24 when the rod locking fastener 24 engages the fixation rod 12 (FIG. 10) to secure the rod 12 in the channel 22 (FIG. 10). The fixation rod 12 can exert a load L onto the rod locking fastener 24 that extends along an axis of the body 24a of the rod locking fastener 24. The load L placed on the rod locking fastener 24 by the fixation rod 12 can cause a reaction force R on the threads 51 of the threaded portions 50 of the base 18 (FIG. 10) which tends to push the side walls 46, 48 of channel 22 away from each other. This reaction force R can displace one or both of the side walls 46, 48 a sufficient amount such that the threads 51 of the threaded portions 50 of one or both of the side walls 46, 48 can separate enough from the thread 52 of the rod locking fastener 24 to allow the fixation rod 12 to move within or disengage from the channel 22.

Preferably, one of a plurality of alternative thread configurations are substituted for the conventional thread configuration on rod locking fastener 24 (FIG. 10) and the threaded portions 50 (FIG. 10) of the side walls 46, 48 (FIG. 10). These alternative thread configurations are shown and described with reference to FIGS. 11A, 11B and 12A–12D.

Figure 11A:
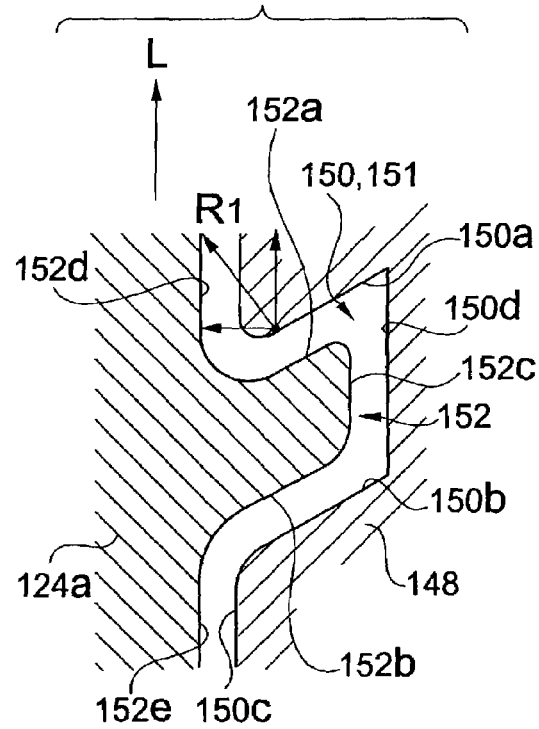
FIG. 11A and 11B are enlarged views of Area 11 of FIG. 10 showing alternate embodiments of the rod locking fastener thread configuration according to the present invention.

FIG. 11A illustrates a first alternate embodiment of the thread and is an enlarged cross-section taken from the same section as Section 11 in FIG. 10 but having a different configuration. In FIG. 11A, a thread 152 extending along the body 124a of the rod locking fastener is shown engaging a corresponding mating thread 151 of the threaded portion 150. The edges of the thread 152 and the threads 151 can be sharp or slightly rounded. It is to be understood that the gap between the thread 152 and the thread 151 is exaggerated for purposes of illustration only. The thread 152 includes a first face 152a, a second face 152b generally parallel to the first face 152a, a third face 152c extending from the first face 152a to the second face 152b, and a root (indicated at 152d and 152e) abutting the first face 152a and the second face 152b. The first face 152a extends at an acute angle from an abutting first portion 152d of the root, the second face 152b extends at an obtuse angle from an abutting second portion 152e of the root, and the third face 152c and the root portions 152d, 152e extend generally parallel to the axis of the body 124a such that, in the illustrated cross-section, the thread 152 has a generally rhomboidal shape. The threads 151 of the threaded portions 150 include a mating generally rhomboidal cross-sectional shape having a first face 150a engaged by the first face 152a of the thread 152, a second face 150b engaged by the second face 152b of the thread 152 and an abutting portion 150d of the root engaged by the third face 152c of the thread 152. The first face 150a extends at an acute angle from an abutting portion 150d of the root, the second face 150b extends at an obtuse angle from the abutting portion 150d of the root, and a third face 150c and the abutting portion 150d of the root extend generally parallel to the axis of the body 124a.

The orientation at an acute angle of the first face 152a and the complimentary orientation of the first face 150a of the threaded portion 150 can prevent unintentional disengagement of the rod locking fastener 24 from the base 18 (FIG. 10). The load L induced on the rod locking fastener 24 (FIG. 10) by the rod 12 (FIG. 10) causes a reaction force R1 perpendicular to the mating first face 150a of the threaded portion 150 that is directed at an angle toward the axis of the body 124a of the rod locking fastener as viewed in FIG. 11A. This direction of the reaction force R1 tends to draw the side walls (only side wall 148 is shown) toward the axis of the body 124a of the rod locking fastener instead of pushing the side walls away as in FIG. 11. Advantageously, the reaction force R1 also increases the frictional force acting between the first face 150a of the threaded portion 150 and the mating first face 152a on the thread 152 such that the force necessary to unscrew the rod locking fastener from the thread portions 150 is increased and discourages the rod locking fastener from backing out of, i.e., unscrewing from, the threaded portions 150. By drawing the side walls (only side wall 148 is shown) toward each other and by increasing the frictional force between the mating faces 150a, 152a, the thread 152 cooperates with the thread of each threaded portion 150 to resist the load L exerted by the fixation rod 12 (FIG. 10) onto the rod locking fastener 24 when the fixation rod 12 is secured in the channel 22 (FIG. 10). Thereby, unintentional disengagement of the fixation rod 12 from the connector 14 can be prevented when the rod locking fastener 24 is subjected to the load L exerted by the fixation rod 12.

Figure 11B:
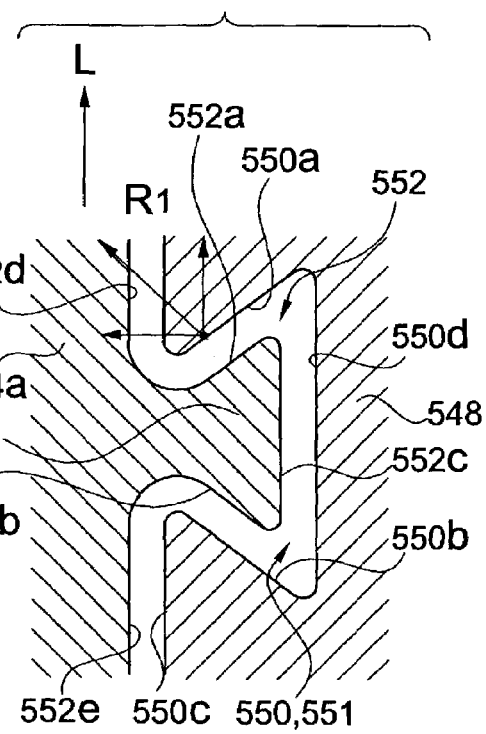

FIG. 11B illustrates a second alternate embodiment of the thread and is an enlarged cross-section taken from the same section as Section 11 in FIG. 10 but with yet another different configuration. In FIG. 11B, a portion of a thread 552 extending along the body 524a of the rod locking fastener engages a corresponding mating thread 551 of the threaded portion 550. The edges of the thread 552 and the threads 551 of the threaded portion 550 can be sharp or slightly rounded. It is to be understood that the gap between the thread 552 and the thread 551 of the threaded portion 550 is exaggerated for purposes of illustration only. The thread 552 includes a first face 552a, a second face 552b extending at angle to the first side 552a, a third side 552c extending from the first side 552a to the second side 552b, and a root 552d, 552e abutting the first face 552a and the second face 552b, respectively. The first face 552a extends at an acute angle from an abutting first portion 552d of the root, the second face 552b extends at an acute angle from an abutting second portion 552e of the root, and the third face 552c and the root portions 552d, 552e extend generally parallel to the axis of the body 524a such that, in the illustrated cross-section, the thread 552 has a generally trapezoidal or generally dovetail shape. The first side 552a extends from the abutting portion 552d of the root at an acute angle and the second face 552b extends from the abutting portion 552e of the root at an acute angle, such that the first face 552a and the second face 552b diverge outwardly from the center of the rod locking fastener. The threads 551 of the threaded portions 550 include a mating generally trapezoidal or generally dovetail shape having a first face 550a engaged by the first face 552a of the thread 552, a second side 550b engaged by the second face 552b of the thread 552, and a root 550d engaged by the third face 552c of the thread 552. The first face 550a extends at an acute angle from an abutting portion 550d of the root, the second face 550b extends at an acute angle from the abutting portion 550d of the root, and a third face 550c and the abutting portion 550d of the root extend generally parallel to the axis of the body 524a.

The orientation at an acute angle of the first face 552a and the complimentary orientation of the mating first surface 550a of the threaded portion 550 can prevent unintentional disengagement of the rod locking fastener 24 from the base 18 (FIG. 10). The load L induced on the rod locking fastener 24 (FIG. 10) by the rod 12 (FIG. 10) causes a reaction force R1 at the mating first side 550a of the threaded portion 550 that is directed at an angle toward the axis of the body 524a of the rod locking fastener as viewed in FIG. 11B. This direction of the reaction force R1 tends to draw the side walls (only side wall 548 is shown) toward the axis of the body 524a of the rod locking fastener instead of pushing the side walls away as in FIG. 11. Additionally, the second side 552b of the thread obstructs deflection of the side walls in a direction away from the rod locking fastener because the second side 550b of the threaded portion 550 will abut the second side 552b of the thread 552 upon such outward deflection. Advantageously, the reaction force R1 also increases the frictional force acting between the first surface 552a and the mating first surface 550a on the threads 552 such that the force necessary to unthread the rod locking fastener from the thread portions 550 increases and discourages the rod locking fastener from backing out of engagement with the threaded portions 550. By drawing the side walls (only side wall 548 is shown) toward each other, by obstructing deflection of the walls away from each other, and by increasing the frictional force between the mating sides 550a, 552a, 550b, 552b, the threads 552 cooperate with the threads of the threaded portion 550 to resist the load L exerted by the fixation rod 12 (FIG. 10) onto the rod locking fastener 24 when the fixation rod 12 is secured in the channel 22 (FIG. 10). Thereby, unintentional disengagement of the fixation rod 12 from the connector 14 can be prevented when the rod locking fastener is subjected to the load L exerted by the fixation rod 12.

Figure 12A:
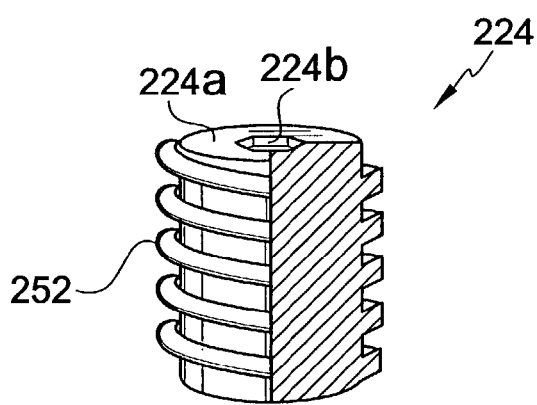
FIGS. 12A–12D are partial cut-away perspective views of alternate embodiments of thread configurations of a rod locking fastener according to the present invention.
Figure 12B:
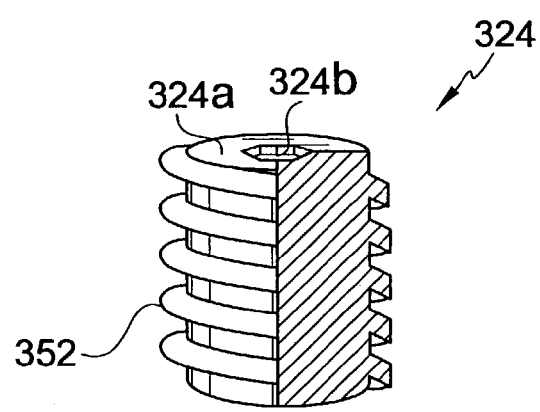
Figure 12C:
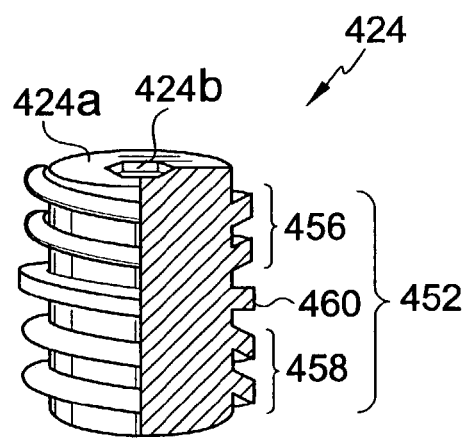

FIGS. 12A–12C illustrate various orientations of the thread for the rod locking fastener described above with reference to FIG. 11A. The threads of the threaded portions of the side walls are not illustrated for clarity, but it is to be understood that they have a complementary mating configuration. In FIG. 12A, the rod locking fastener 224 includes a body 224a, a thread 252 extending along the body, and a tool engagement portion 224b. The thread 252 is oriented in the same configuration as the thread 152 described above with reference to FIG. 11A and mates with threads formed in the thread portions of the base of the connector. The tool engagement portion 224b (as shown) is configured for engagement by a standard tool, such as a screw driver or a wrench. A hex head configuration is shown.

In FIG. 12B, the orientation of the thread is reversed relative to FIG. 12A. The rod locking fastener 324 of FIG. 12B includes a body 324a extending along an axis, a thread 352 extending along the body, and a tool engagement portion 324b. The thread 352 has a first surface (not numbered) extending at an acute angle and a second surface extending at an obtuse angle, as described above with reference to FIG. 11A, except that the first surface is the lower surface of the thread 352 and the second surface is the upper surface of the thread 352. The orientation of the threads 352 of FIG. 12B can be advantageous in a system where the load L is oriented in the opposite direction to that shown in FIG. 11A. The tool engagement portion 324b (as shown) is configured for engagement by a standard tool, such as a screw driver or a wrench. A hex head configuration is shown.

In FIG. 12C, the rod locking fastener 424 includes a body 424a extending along an axis, a thread 452 extending along the body 424a, and a tool engagement portion 424b. The thread 452 includes three thread portions 456, 458, 460. The first thread portion 456 has the first face portion (not numbered) extending at an acute angle and a the second face portion (not numbered) extending at an obtuse angle with same orientation relative to the body 424a as that described with reference to FIGS. 11A and 12A, above. The third thread portion 458 has the first face portion (not numbered) extending at an obtuse angle and the second face (not numbered) extending at an acute angle with the same orientation relative to the body 424a as that described with reference to FIG. 12B, above. And, the second thread portion 460 can be intermediate the first thread portion 456 and the third thread portion 458. The second thread portion 460 can be configured as a flat thread portion having the first face (not numbered) and the second face (not numbered) extending substantially perpendicular from the respective abutting portion of the root. The first face and the second face of the thread 452 preferably have a smooth transition from the first portion (at 456) to the second portion (at 460) and from the second portion (at 460) to the third portion (at 458). The first thread portion 456 and the third thread portion 458 provide the functions as described above with reference to FIGS. 11A, 12A and 12B such that the mating faces of the threads 452 and the threaded portions (not shown) can cooperate to resist a load L exerted by fixation rod 12 (FIG. 10). The second thread portion 460 provides additional frictional engagement with the mating thread of the threaded portion (not shown, see, for example 551 in FIG. 11B). Although not shown for this embodiment, the mating threads in the threaded portion could be configured in a trapezoidal or dovetail shape similar to that shown and described with reference threaded portion 550 in FIG. 11B, above, to accommodate the three different thread portions 456, 458, 460. The tool engagement portion 424*b* (as shown) is configured for engagement by a standard tool, such as a screw driver or a wrench. A hex head configuration is shown.

Figure 12D:
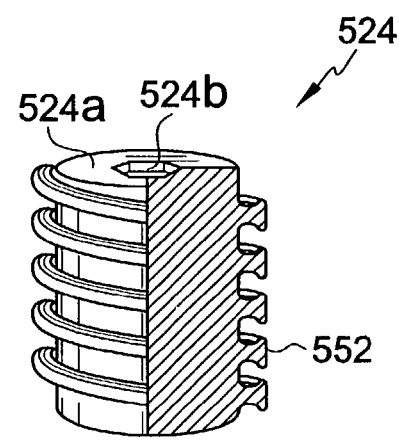

FIG. 12D illustrates another alternate embodiment of a rod locking fastener 524 having body 524*a* extending along an axis, a thread 552 extending along the body 524*a*, and a tool engagement portion 524*b*. The thread 552 is configured as a trapezoidal or dovetail thread as described above with reference to FIG. 11B, such that the thread 552 includes a first face 552*a* (FIG. 11B) extending at an acute angle with respect to the abutting first portion 552*d* (FIG. 11B) of the root along the entire length of the thread 552 and a second face 552*b* (FIG. 11B) extending at an acute angle with respect to the abutting second portion 552*e* (FIG. 11B) of the root along the entire length of the thread 552. Similar to the three separate thread portions 456, 458, 460 described above with reference to FIG. 12C, the first face 552*a* and the second face 552*b* cooperate with the mating faces 550*a*, 550*b* (FIG. 11B) of the threaded portion 550 (FIG. 11B) to resist a load L exerted by fixation rod 12 (FIG. 10). The threads of the threaded portions of the side walls are not illustrated for clarity, but it is to be understood that they have a mating configuration as shown in FIG. 11B. The tool engagement portion 524*b* (as shown) is configured for engagement by a standard tool, such as a screw driver or a wrench. A hex head configuration is shown.

Although, the thread configurations of FIGS. 11A–12D are described above in the context of a spinal alignment system, each of these thread configurations could be used in other surgically implantable systems having mating parts or requiring a secure locking mechanism. Further, each of the thread configurations described herein can be used by fasteners, such as machine screws, bolts and nuts, or to provide threaded connections to secure two or more components together outside the medical field. And, if used in situations without mating parts, these thread configurations could be configured to have a self-tapping thread along part of or the entire length of the thread. Additionally, the thread configurations described herein can be arranged in a single helix or in a multiple helix configuration.

Figure 13:
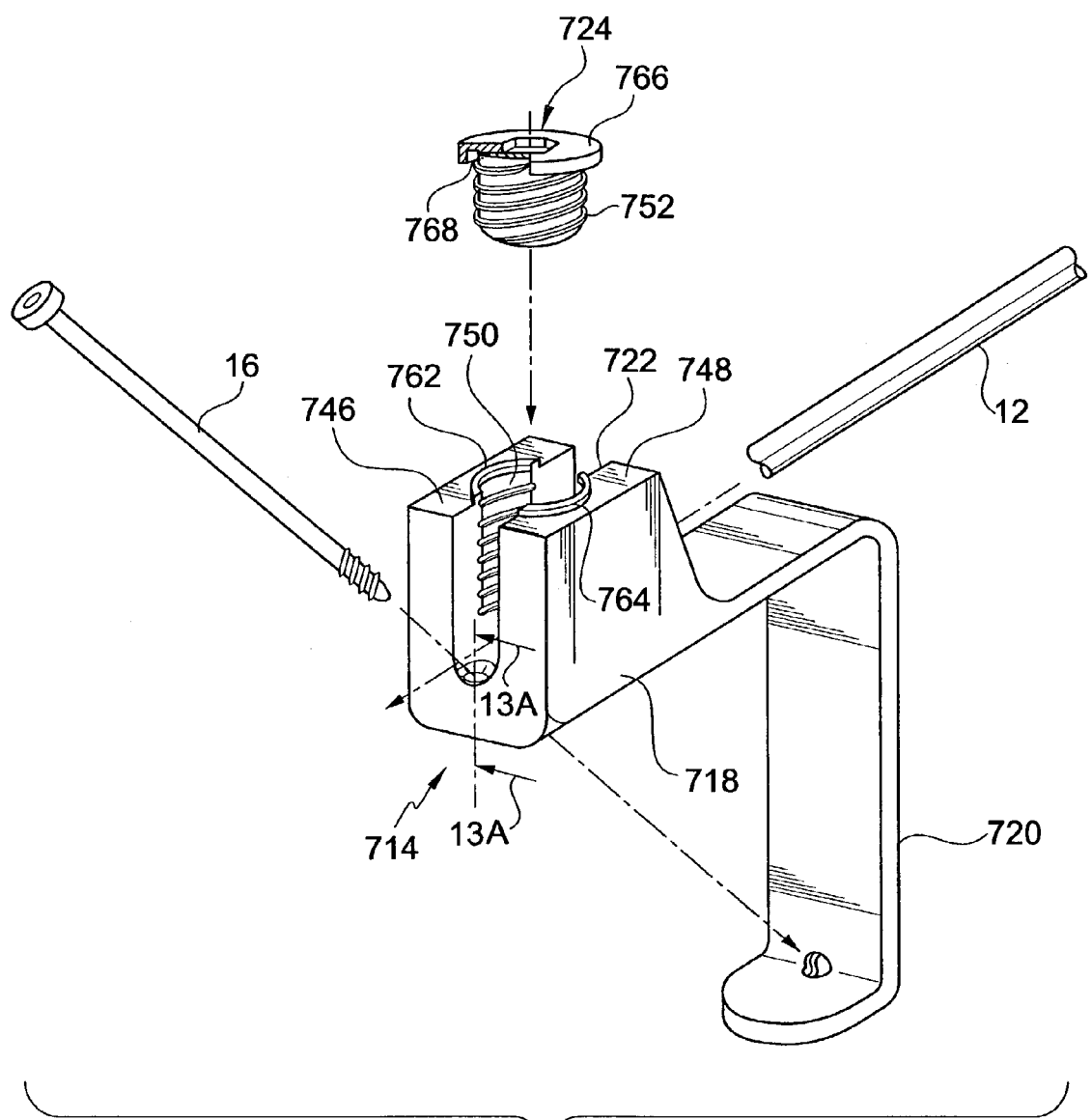
FIG. 13 is an exploded perspective view of another embodiment of a connector and a rod locking fastener of a spinal alignment system according to the present invention.
Figure 13A:
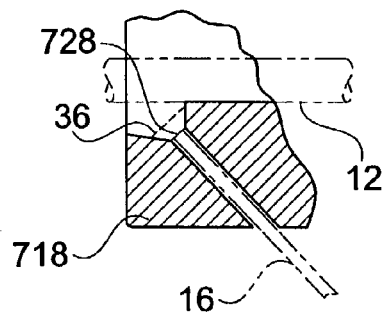
FIG. 13A is an enlarged partial cross-sectional view taken along line 13A—13A of FIG. 13.

FIG. 13 illustrates an eighth embodiment of the connector 714 that includes a base 718 and a hook 720. The base 718 includes a channel 722 that receives the fixation rod 12. The channel 722 forms a first side wall 746 and a second side wall 748. Each side wall 746, 748 includes a threaded portion 750 facing the channel 722 and an arcuate ridge 762, 764 at the top of the side walls 746, 748 aligned with the threaded portions 750. A rod locking fastener 724 includes threads 752 and a head 766. The threads 750, 752 can be conventional threads or configured as described above with reference to FIGS. 11–12D. The head 766 includes an annular groove 768 in the bottom surface of the head. The annular groove 768 engages the arcuate ridges 762, 764 when the rod locking fastener 724 is threaded into the channel 722 against the fixation rod 12. The mating engagement between the arcuate ridges 762, 764 and the annular groove 768 resists separation of the side walls 746, 748 away from each other. Alternatively, an annular groove can be provided at the top of the side walls 746, 748 and aligned with the threaded portions and an annular ridge can be provided in the bottom surface of the head 766. Thus, the annular groove(s) cooperates with the annular ridge(s) to resist the load L (FIG. 12A) exerted by the fixation rod 12 onto the rod locking fastener 724 when the fixation rod 12 is secured in the channel 722.

Figure 14:
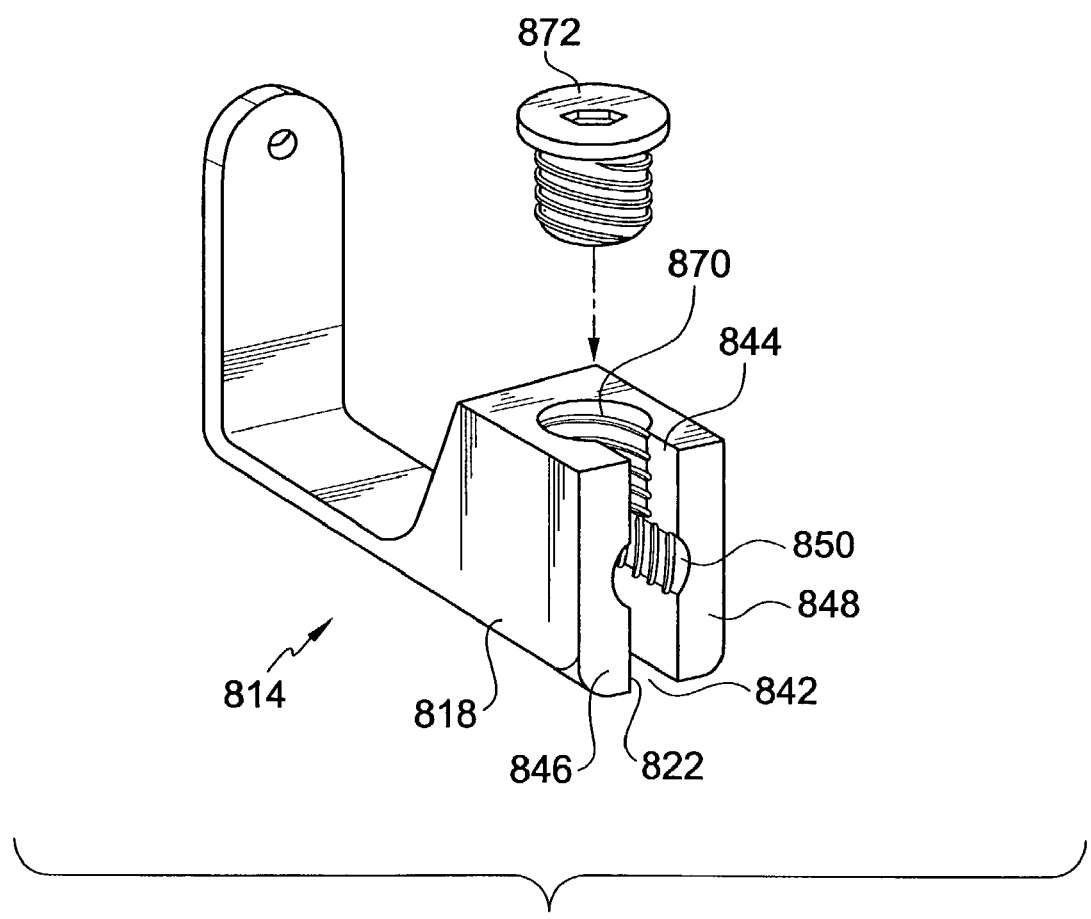
FIG. 14 is a perspective view of another embodiment of a connector of a spinal alignment system according to the present invention.
Figure 15:
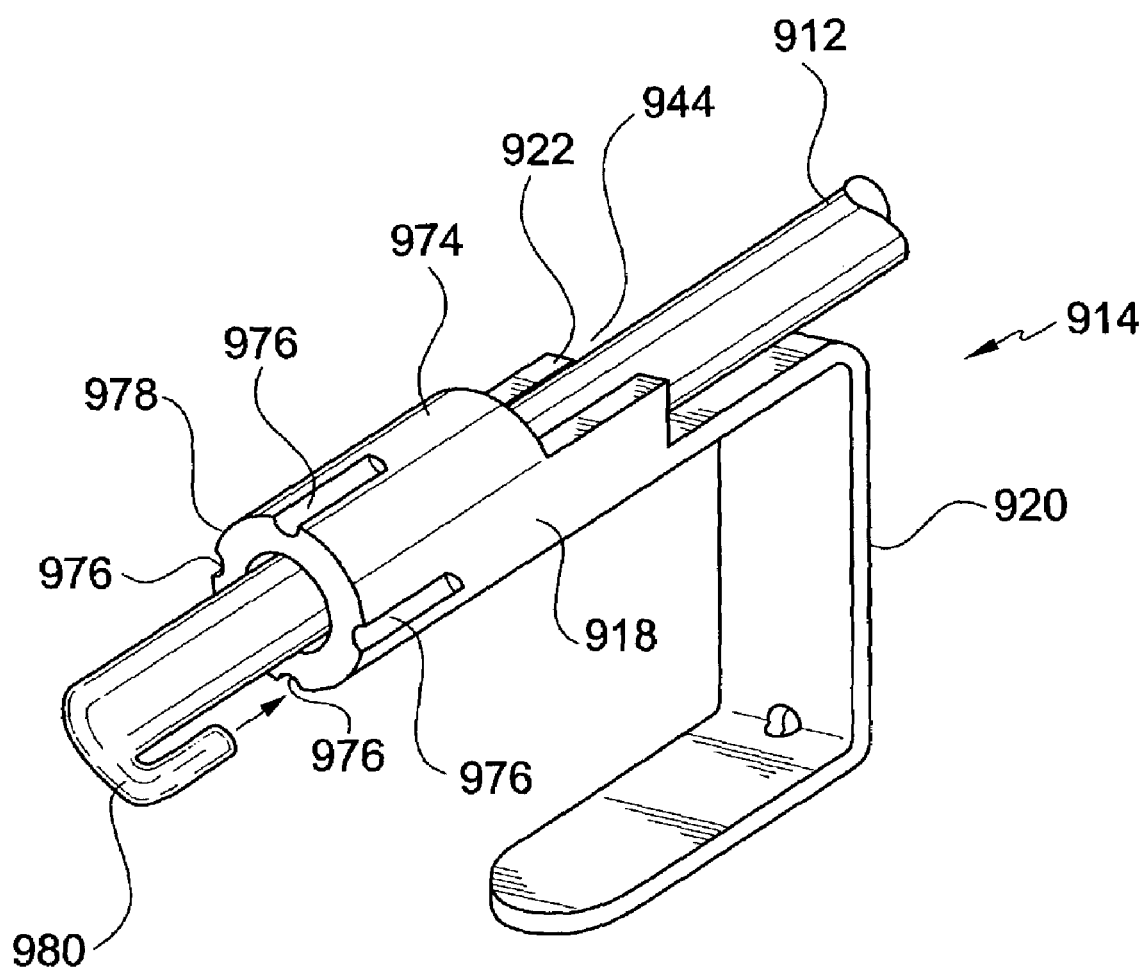
FIG. 15 is a perspective view of a another embodiment of a connector and a fixation rod of a spinal alignment system according to the present invention.

Referring now to FIGS. 14 and 15, embodiments of the connector and the fixation rod that block movement of the fixation rod in the channel of the connector will be now described. FIG. 14 shows an embodiment of the present invention in which longitudinal displacement of the fixation rod is blocked. FIG. 15 shows an embodiment of the present invention in which the fixation rod and the connector cooperate to block rotational motion of the fixation rod in the channel of the connector as well as block longitudinal displacement of the fixation rod.

FIG. 14 shows a connector 814 that includes a base 818 having a channel 822. The channel 822 receives a fixation rod (not shown) and forms two side walls 846, 848. The side walls 846, 848 include first threaded portion 850 and a second threaded portion 870. The first threaded portions 850 engage a rod locking fastener (not shown) to secure the fixation rod (not shown) in the channel 822. The second threaded portion 870 is located adjacent a second open end 844 of the channel 822. A rod locating fastener 872 is threaded into the second open end 844 of the channel 822 by way of the threaded portions 870 so that the end of the rod locating fastener 872 abuts the end of the fixation rod (not shown) and blocks displacement of the fixation rod out of the second open end 844 along the longitudinal axis of the fixation rod. This feature would only be used on the end connectors of the system 10.

Alternatively, other configurations of the channel and the base can be used to block displacement of the fixation rod along its longitudinal axis. In one such alternative embodiment, the channel can be formed in the base to have one open end and one closed end. In another such embodiment, a plug can be press fit into the second open end of the channel. Instead of a friction fit, the plug can be fit with a morse taper into the second open end of the channel of an end connector.

In the embodiment of the FIG. 15, a connector 914 includes a base 918 and a hook 920. The base 918 includes a channel 922 and a hollow section 974 aligned with the channel 922. The channel includes a first open end (not numbered) open to the hollow section 974 and a second open end 944. A fixation rod 912 is inserted through the hollow section 974 into the channel 922 to extend beyond the second open end 944. The hollow section 974 is dimensioned slightly larger than the transverse cross-section dimensioning of a fixation rod 912 so that the fixation rod can slide into the hollow section 974 while blocking excessive tilting movement of the fixation rod 912. Preferably, the hollow section 974 and the fixation rod are cylindrical. Alternatively, the hollow section and the fixation rod can be polygonal. Mating polygonal geometrical configurations of the hollow section 974 and the fixation rod 912 can block rotational motion of the fixation rod 912 within the channel 922.

A plurality of grooves 976 are formed adjacent the end 978 of the hollow section furthest from the channel 922. The fixation rod 912 includes an U-shaped end 980 that is received in one of the grooves 976. The U-shaped end 980 and the engaged groove 976 cooperate to block rotational movement of the fixation rod 912 within the channel 922. Alternatively, the grooves can be oriented to extend orthogonal to the fixation rod and the fixation rod can have one or more orthogonal projections extending from the end of the fixation rod that engage a respective one of the orthogonal grooves such that rotational movement of the fixation rod within the channel is blocked.

FIGS. 16–17B illustrate another embodiment of a bone fastener in the form of an expandable pin 116 that includes two resiliently expandable L-shaped portions 116a instead of threads. Each L-shaped portion includes a foot 116b extending radially outwardly from the expandable pin 116. Preferably, the bottom of each foot 116b is rounded. A slotted through bore 930 is provided in the junction of the first hook portion 932 and the second hook portion 934 of the connector 914. The resiliently expandable portions 116a are squeezed together and then inserted through the guide aperture 928 and toward the slotted bore 930. The head 136 of the expandable pin 116 is configured to be drivingly engaged by a tool to rotate feet 116b into alignment with slots 930a in the slotted bore 930 such that the feet 116b can pass completely through the slotted bore 930. The feet 116b and the slots 930a provide tactile input to the surgeon so that the feet 116b can be aligned with the slots 930a. In order to avoid puncturing the surgeon's gloves, or damaging adjacent tissue, the feet 116b and the slots 930a should not be sharp or pointed.

After the feet 116b have passed through the slotted bore 930, the expandable pin 116 is rotated so that the feet 116b are out of alignment with the slots 930a. Referring to FIGS. 17A and 17B, the feet 116b slide along arcuate grooves 930b extending from the slots 930a as the pin 116 is rotated. Each groove 930b is in communication with a respective one of the slots 930a. A stop 930c is formed at the end of each groove 930b adjacent the other of the slots 930a to prevent over-rotation of the feet 116b into the other of the slots 930a and to provide positive feedback that the feet 116a have been sufficiently rotated out of alignment with the slots 930a. The grooves 930b can have a constant depth or a tapered depth that increases toward the stop 930c. The arcuate extent of the grooves 930b can be made shorter and the stops 930c positioned relative to the slots 930a such that the stops 930c permit only a quarter-turn or a third-turn of the pin 116, instead of the preferred half-turn illustrated in FIG. 17A. It is within the scope of the invention, however, to provide alternative arrangements that can limit the amount of rotation of the pin 116 and to minimize the exposure of the feet 116b against surrounding tissue.

The L-shaped portions 116a are biased into frictional engagement with the slotted bore 930 such that unintended rotation of the pin 116 is prevented. The head 136 and the feet 116b cooperate to with the base 918 and the hook 920 to secure the pin 116 in the fastener 914. As in the embodiments of FIGS. 2–8 discussed above, the pin 116 and the connector 914 cooperate to lock the connector to the vertebra. If removal of the pin 116 is desired, then the pin 116 is rotated until the feet 116b align with the slots 930a. Consequently, the pin 116 can then be pulled away from the slotted bore 930.

Although the invention has been described for use in correcting a human spine, the system 10 can be used for other orthopedic procedures in other boney areas. Furthermore, the system can be used with bone structures other than human bone structures.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What we claim is:

1. A spinal alignment system including:
   a connector adapted to engage a vertebra of a human spinal column, the connector comprising:
   a base having a channel;
   a hook extending from the base;
   a guide aperture extending through one of the base member and the hook member; and
   a locking portion being located in another one of the base member and the hook member, the locking portion being coaxial with the guide aperture;
   a bone fastener including a head and a shaft extending from the head, the guide aperture cooperating with the shaft to guide the bone fastener through the vertebra in alignment with the locking portion when the bone fastener is inserted into the guide aperture, and the locking portion engaging the shaft when the bone fastener is inserted into the vertebra;
   a fixation rod; and
   a rod locking fastener cooperating with the channel to secure the fixation rod to the connector when the fixation rod is received in the channel and the rod locking fastener is engaged with the channel.

2. The spinal alignment system according to claim 1, wherein the connector is adapted to engage an anterior portion of the vertebra.

3. The spinal alignment system according to claim 1, wherein the channel is detachable from the hook.

4. The spinal alignment system according to claim 1, wherein the bone fastener is a pin.

5. The spinal alignment system according to claim 1, wherein when the bone fastener is tightly received in the locking portion, the bone fastener is placed in tension and the connector is placed in compression such that the bone fastener and the connector cooperate to define a tension band that distributes a force exerted by the fixation rod throughout the connector and the bone fastener.

6. The spinal alignment system according to claim 1, wherein the rod locking fastener and the base include mating surfaces that cooperate with each other to resist a force exerted by the fixation rod onto the rod locking fastener when the fixation rod is secured in the channel.

7. The spinal alignment system according to claim 6, wherein the mating surfaces comprise threads formed on the rod locking fastener and in the channel.

8. The spinal alignment system according to claim 7, wherein the mating surfaces further comprise one of an arcuate groove and an arcuate ridge on each side of the channel and another one of an arcuate groove and an arcuate ridge on the rod locking fastener.

* * * * *